US009585697B2

(12) United States Patent
Stachniak

(10) Patent No.: US 9,585,697 B2
(45) Date of Patent: Mar. 7, 2017

(54) POSTERIOR STABILIZATION SYSTEMS AND METHODS

(71) Applicant: Rebecca Elizabeth Stachniak, Plano, TX (US)

(72) Inventor: Rebecca Elizabeth Stachniak, Plano, TX (US)

(73) Assignee: Rebecca Elizabeth Stachniak, Plano, TX (US)

( * ) Notice: Subject to any disclaimer, the term of this patent is extended or adjusted under 35 U.S.C. 154(b) by 380 days.

(21) Appl. No.: 14/043,188

(22) Filed: Oct. 1, 2013

(65) Prior Publication Data

US 2014/0249581 A1    Sep. 4, 2014

Related U.S. Application Data

(63) Continuation-in-part of application No. PCT/US2012/031922, filed on Apr. 2, 2012.

(60) Provisional application No. 61/708,384, filed on Oct. 1, 2012, provisional application No. 61/470,885, filed on Apr. 1, 2011.

(51) Int. Cl.
*A61B 17/70* (2006.01)
*A61B 17/80* (2006.01)

(52) U.S. Cl.
CPC ...... *A61B 17/7035* (2013.01); *A61B 17/7044* (2013.01); *A61B 17/7083* (2013.01); *A61B 17/8085* (2013.01); *A61B 17/7032* (2013.01); *A61B 17/7034* (2013.01); *A61B 17/7041* (2013.01); *A61B 17/809* (2013.01)

(58) Field of Classification Search
CPC ............ A61B 17/7041; A61B 17/7035; A61B 17/7032; A61B 17/7034; A61B 17/7044
See application file for complete search history.

(56) References Cited

U.S. PATENT DOCUMENTS 5,470,333 A * 11/1995 Ray ..................... A61B 17/7055
606/261
5,545,164 A * 8/1996 Howland ........... A61B 17/7055
606/250

(Continued)

FOREIGN PATENT DOCUMENTS

EP    1967150 A1    9/2008

OTHER PUBLICATIONS

International Search Report and Written Opinion received in Patent Cooperation Treaty Application No. PCT/US2013/062883, dated Mar. 13, 2014, 15 pages.

*Primary Examiner* — Mary Hoffman
(74) *Attorney, Agent, or Firm* — Haynes and Boone, LLP

(57) ABSTRACT

An implantable body for a posterior stabilization system includes a lateral end, a medial end, an inwardly facing surface configured to abut against a lamina when the body is implanted along a vertebra. A lateral bone outrigger extends from the inwardly facing surface and may include a bone-abutting surface along a medial portion disposed to abut against a lateral mass of the vertebra when the body is implanted along a vertebra. The lateral bone outrigger may have a first height. A penetrating feature extends from the inwardly facing surface between the bone-engaging portion of the inwardly facing surface and the lateral bone outrigger. The penetrating feature may have a second height less than the first height. A fastener bore extends through the body at an angle toward the lateral bone outrigger.

20 Claims, 29 Drawing Sheets

(56) References Cited

U.S. PATENT DOCUMENTS

| | | | | |
|---|---|---|---|---|
| 5,549,612 A * | 8/1996 | Yapp | A61B 17/7059 411/200 |
| 5,735,852 A * | 4/1998 | Amrein | A61B 17/7044 606/278 |
| 5,928,233 A * | 7/1999 | Apfelbaum | A61B 17/7055 606/261 |
| 6,106,526 A * | 8/2000 | Harms | A61B 17/7041 606/264 |
| 6,533,787 B1 * | 3/2003 | Lenke | A61B 17/7008 606/75 |
| 8,894,685 B2 * | 11/2014 | Mickiewicz | A61B 17/7064 606/247 |
| 9,044,277 B2 * | 6/2015 | O'Neil | A61B 17/7064 |
| 2004/0111161 A1 | 6/2004 | Trieu | |
| 2004/0162558 A1 * | 8/2004 | Hegde | A61B 17/7044 606/287 |
| 2006/0116676 A1 * | 6/2006 | Gradel | A61B 17/7041 606/278 |
| 2006/0149373 A1 * | 7/2006 | Winslow | A61F 2/4405 623/17.11 |
| 2006/0149374 A1 * | 7/2006 | Winslow | A61F 2/4405 623/17.11 |
| 2006/0247633 A1 * | 11/2006 | Winslow | A61B 17/025 606/247 |
| 2006/0247650 A1 | 11/2006 | Yerby et al. | |
| 2009/0177237 A1 * | 7/2009 | Zucherman | A61B 17/7059 606/280 |
| 2009/0318968 A1 * | 12/2009 | Duggal | A61B 17/7026 606/250 |
| 2010/0087869 A1 | 4/2010 | Abdou | |
| 2011/0098747 A1 * | 4/2011 | Donner | A61B 17/70 606/264 |
| 2012/0271359 A1 * | 10/2012 | Stevenson | A61B 17/7071 606/281 |
| 2014/0249581 A1 * | 9/2014 | Stachniak | A61B 17/7035 606/264 |
| 2016/0015430 A1 * | 1/2016 | Buttermann | A61B 17/7032 606/276 |

* cited by examiner

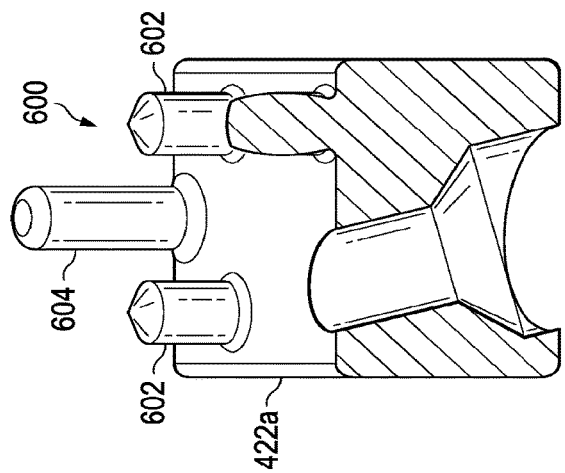
Fig. 18E
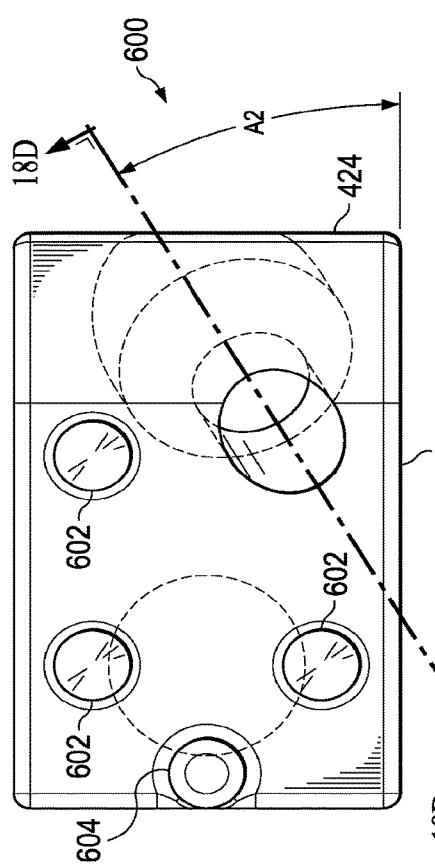
Fig. 18C
Fig. 18D
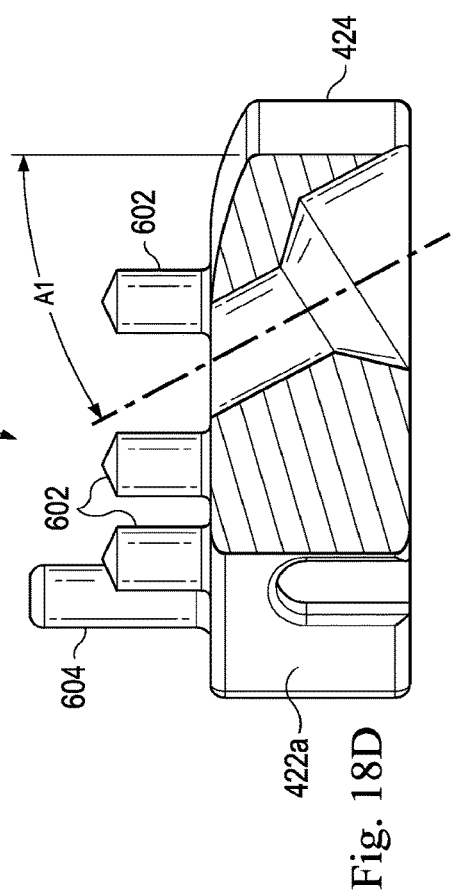

POSTERIOR STABILIZATION SYSTEMS AND METHODS

PRIORITY

This patent application claims priority to and the benefit of the filing date of U.S. Provisional Patent Application 61/708,384, filed Oct. 1, 2012, titled "Posterior Stabilization System and Method," which is incorporated herein by reference. This patent application also claims priority to and is a continuation in part application of International Application PCT/US2012/031922, filed Apr. 2, 2012, titled "Posterior Cervical Stabilization System and Method," which claims priority to and the benefit of the filing date of U.S. Provisional Patent Application 61/470,885, filed Apr. 1, 2011, both of which are incorporated herein by reference.

FIELD OF THE INVENTION

The present disclosure relates to devices, systems, and methods for stabilizing posterior elements of the spine. More particularly, the disclosure relates to posterior stabilization devices, systems, and methods that may secure to the cervical and thoracic spine.

BACKGROUND

The vertebrae in a patient's spinal column are linked to one another by the disc, ligaments and the facet joints. The facet joints control movement of the vertebrae relative to one another. Each vertebra has a pair of articulating surfaces located on the left or right side, and each pair includes a superior articular process and an inferior articular process. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Facet joints and/or discs that become diseased, degenerated, impaired, or otherwise painful can require surgery to stabilize the joint. Traditionally, diseased levels in the spine were fused to one another. While such a technique may relieve pain, the fusing effectively prevents motion between at least two vertebrae. As a result of the limited motion, additional stress may be applied to the adjoining levels, thereby potentially leading to further damage to the spine.

Multiple techniques have been used in the past to stabilize the spine, including the cervical spine, from a posterior approach to the boney elements. Such approaches have included minimally invasive techniques. Despite these attempts, there remain difficulties in safe placement of existing fixation devices, particularly on small cervical bones, as well as difficulties in achieving solid fixation with minimal disruption to surrounding tissue.

The present disclosure is directed to devices, systems, and methods that address one or more deficiencies in the prior art.

SUMMARY

According to various aspects of the disclosure, a posterior stabilization system may be secured to associated occipital $C_1$, $C_2$, and thoracic spine portions. The system may be modular such that it can be attached to the skull or, using fluoroscopic imaging, can be placed at $C_1$ $C_2$. The system may include jigs or modules configured for use primarily with the lateral masses of the cervical spine $C_3$-$C_6$ or, with the secured variation, for use with the $C_7$ pedicles or the thoracic pedicles. Thus, the system could be used from the skull through the Tspine.

The $C_3$-$C_6$ lateral mass modules would contain a pre-drilled hole with orientation of about 20-40° laterally (away from the spinal cord) and rostrally about 20-40° (toward the head). The module can be held by an introducer instrument as a fork device (e.g., top-loading) that can secure the position of the jig or module in conjunction with tiny spikes on the bottom of the modules prior to holes being drilled in the bone, for example, with a tap, and final fixation with a screw, such as a titanium screw. The modules can be secured to a rod laterally with top loading nuts. The lateral mass modules could then be secured to occipital $C_1$, $C_2$, $C_7$ thoracic with screws. The $C_7$ or thoracic modules are oriented with pre-drilled holes about 10-15° medially.

In an exemplary aspect, the present disclosure is directed to a posterior stabilization system that includes a rod; a plurality of modules configured to be coupled with the rod, each of the modules including a pre-drilled hole for providing a predetermined orientation for a screw to be associated with the module; and a screw associated with each module, the screws extending through the respective modules and extending from the module in said predetermined orientation. In one aspect, the system includes a plurality of securing members, each securing member cooperating with one of said modules to fixedly position the module on the rod.

In another exemplary aspect, the present disclosure is directed to an implantable body for a posterior stabilization system that includes a lateral end, a medial end, an inwardly facing surface, and an outwardly facing surface. The inwardly facing surface has a bone-abutting portion disposed proximate the medial end and configured to abut against a lamina when the body is implanted along a vertebra. The system also includes a lateral bone outrigger extending from the inwardly facing surface adjacent the lateral end. The lateral bone outrigger has a bone-abutting surface along a medial portion disposed to abut against a lateral mass of the vertebra when the body is implanted along a vertebra. The lateral bone outrigger has a first height. A penetrating feature extends from the inwardly facing surface between the bone-engaging portion of the inwardly facing surface and the lateral bone outrigger. The penetrating feature has a second height less than the first height. A fastener bore extends through the body from the inwardly facing surface to the outwardly facing surface, and is angled toward the lateral bone outrigger.

In an aspect, the inwardly facing surface comprises a tapered surface and a flat surface, the bone-abutting portion being formed of the tapered surface. In an aspect, the inwardly facing surface comprises a curved surface and a flat surface, the bone-abutting portion being formed of the curved surface. In an aspect, the bone-abutting surface on the lateral bone outrigger is a rounded surface. In an aspect, the fastener bore is angled at an angle within the range of about 20-55 degrees when measured in cross-section. In an aspect, the fastener bore is angled at an angle within the range of about 20-55 degrees as measured from a side edge. In an aspect, the second height from the inwardly facing surface is within a range of about 4-8 mm. In an aspect, the lateral bone outrigger is cylindrically shaped and is disposed proximate only a portion of the lateral end. In an aspect, the lateral bone outrigger is disposed in a corner of the inwardly facing surface. In an aspect, the lateral bone outrigger is disposed along a centerline extending from the medial end to the lateral end. In an aspect, the fastener bore is angled so that when the implantable is implanted, the fastener bore forms an angle in the range of 20-55 degrees from the sagittal plane and an angle in the range of 20-55 degrees from the axial plane.

In another exemplary aspect, the present disclosure is directed to a posterior stabilization system that includes an implantable body shaped to abut against a lateral mass of a cervical vertebra. The body includes a lateral end, a medial end, an inwardly facing surface and an outwardly facing surface. The inwardly facing surface has a bone-abutting portion disposed proximate the medial end configured to abut against a lamina when the body is implanted along a vertebra. The body also includes a lateral bone outrigger extending from the inwardly facing surface adjacent the lateral end, the lateral bone outrigger having a bone-abutting surface at along a medial portion disposed to abut against a lateral mass of the vertebra when the body is implanted along a vertebra. The body also includes a penetrating feature extending from the inwardly facing surface between the bone-engaging portion of the inwardly facing surface and the lateral bone outrigger, the penetrating feature having a second height less than the first height; and includes a fastener bore extending through the body from the inwardly facing surface to the outwardly facing surface. The system includes a rod receiving portion sized to receive a fixation rod, the rod receiving portion being pivotably attached to the body and includes a fastener sized to extend through the bore and penetrate the lateral mass of the vertebra.

In an aspect, the inwardly facing surface comprises a tapered surface and a flat surface, the bone-abutting portion being formed of the tapered surface. In an aspect, the inwardly facing surface comprises a curved surface and a flat surface, the bone-abutting portion being formed of the curved surface. In an aspect, the bone-abutting surface on the lateral bone outrigger is a rounded surface. In an aspect, the fastener bore is angled at an angle within the range of about 20-55 degrees when measured in cross-section. In an aspect, the fastener bore is angled at an angle within the range of about 20-55 degrees as measured from a side edge. In an aspect, the lateral bone outrigger has a height above the inwardly facing surface within a range of about 4-8 mm. In an aspect, the lateral bone outrigger is cylindrically shaped and is disposed proximate only a portion of the lateral end. In an aspect, the lateral bone outrigger is disposed in a corner of the inwardly facing surface. In an aspect, the lateral bone outrigger is disposed along a centerline extending from the medial end to the lateral end. In an aspect, the fastener is a bolt. In an aspect, the rod receiving portion is integrally formed with the body. In an aspect, the fastener bore is angled so that when the implantable is implanted, the fastener bore forms an angle in the range of 20-55 degrees from the sagittal plane and an angle in the range of 20-55 degrees from the axial plane.

In another exemplary aspect, the present disclosure is directed to a non-pedicle based fixation system. The system includes a first posterior stabilization system that includes a first body shaped to abut against a lateral mass of a first cervical vertebra, the first body including a lateral end, a medial end, an inwardly facing surface, and an outwardly facing surface, the inwardly facing surface having a bone-abutting portion disposed proximate the medial end and configured to abut against a lamina when the body is implanted along a vertebra; a lateral bone outrigger extending from the inwardly facing surface adjacent the lateral end, the lateral bone outrigger having a bone-abutting surface at along a medial portion disposed to abut against a lateral mass of the vertebra when the body is implanted along a vertebra; and a penetrating feature extending from the inwardly facing surface between the bone-engaging portion of the inwardly facing surface and the lateral bone outrigger, the penetrating feature having a second height less than the first height. A first rod receiving portion is shaped to receive a fixation rod, the rod receiving portion being disposed closer to the lateral end than the medial end. A second posterior stabilization system includes a second body shaped to abut against a lateral mass of a second cervical vertebra, the first body comprising: a lateral end, a medial end, an inwardly facing surface, and an outwardly facing surface, the inwardly facing surface having a bone-abutting portion disposed proximate the medial end and configured to abut against a lamina when the body is implanted along a vertebra; a lateral bone outrigger extending from the inwardly facing surface adjacent the lateral end, the lateral bone outrigger having a bone-abutting surface at along a medial portion disposed to abut against a lateral mass of the vertebra when the body is implanted along a vertebra; a penetrating feature extending from the inwardly facing surface between the bone-engaging portion of the inwardly facing surface and the lateral bone outrigger, the penetrating feature having a second height less than the first height; and a second rod receiving portion shaped to receive the fixation rod, the rod receiving portion being disposed closer to the lateral end than the medial end; and a fixation rod disposed within the first and second rod receiving portions.

In an aspect, the first body comprises a fastener bore extending through the body from the inwardly facing surface to the outwardly facing surface, the fastener bore being angled toward the lateral bone outrigger. In an aspect, the first body includes a side edge, the fastener bore being angled away from the side edge. In an aspect, the fastener bore is angled toward the lateral bone outrigger within an angle range of about 20-55 degrees, and the fastener bore angled away from the side edge within an angle range of about 20-55 degrees.

In another exemplary aspect, the present disclosure is directed to a surgical method comprising: introducing a body portion to a first vertebra so that an inwardly facing surface proximate a medial end abuts a lamina of the vertebra and so that a lateral bone outrigger extending from the inwardly facing surface adjacent the lateral end abuts against a lateral side of the lateral mass of the vertebra; driving a fastener in a lateral direction toward the lateral bone outrigger and into the lateral mass through a fastener bore extending through the body portion; and inserting a fixation rod in a rod receiver associated with the body portion so that the rod is disposed lateral of the fastener bore.

In an aspect, the method includes forming a pilot hole in the lateral mass through the body portion before driving the fastener, the hole being formed in the lateral mass in a direction toward the lateral bone outrigger. In an aspect, the method includes applying loading against the body portion to drive penetrating features on the body portion into the lamina.

In another exemplary aspect, the present disclosure is directed to an implantable body for a posterior stabilization system including a lateral end, a medial end, an inwardly facing surface, and an outwardly facing surface, the inwardly facing surface having a bone-abutting portion disposed proximate the medial end and configured to abut against a lamina when the body is implanted along a vertebra; a lateral bone outrigger extending from the inwardly facing surface adjacent the lateral end, the lateral bone outrigger having a bone-abutting surface at along a medial portion disposed to abut against a lateral mass of the vertebra when the body is implanted along a vertebra, the lateral bone outrigger having a first height; a penetrating feature extending from the inwardly facing surface between the bone-engaging portion of the inwardly facing surface and the lateral bone outrigger, the penetrating feature having a second height less than the first height; and a fastener bore extending through the body from the inwardly facing surface to the outwardly facing surface.

In an aspect, the fastener bore is angled toward the lateral bone outrigger. In an aspect, the fastener bore is angled at an oblique angle.

In some aspects of the systems disclosed herein, the outrigger is angled in the lateral direction from the jig. In some aspects, the inwardly facing surface includes a convex portion and a concave portion, the convex portion being near the medial end and the concave portion being near the lateral end. In some aspects, a head and post extend from the jig, and a receiver is configured to pivot about the head.

Some further advantages and embodiments may become evident from the attached drawings.

BRIEF DESCRIPTION OF THE DRAWINGS

Aspects of the present disclosure are best understood from the following detailed description when read with the accompanying figures.

FIGS. 18A-18E illustrate views of an exemplary jig of the posterior cervical stabilization system in accordance with various aspects of the disclosure.

DETAILED DESCRIPTION

Figure 1:
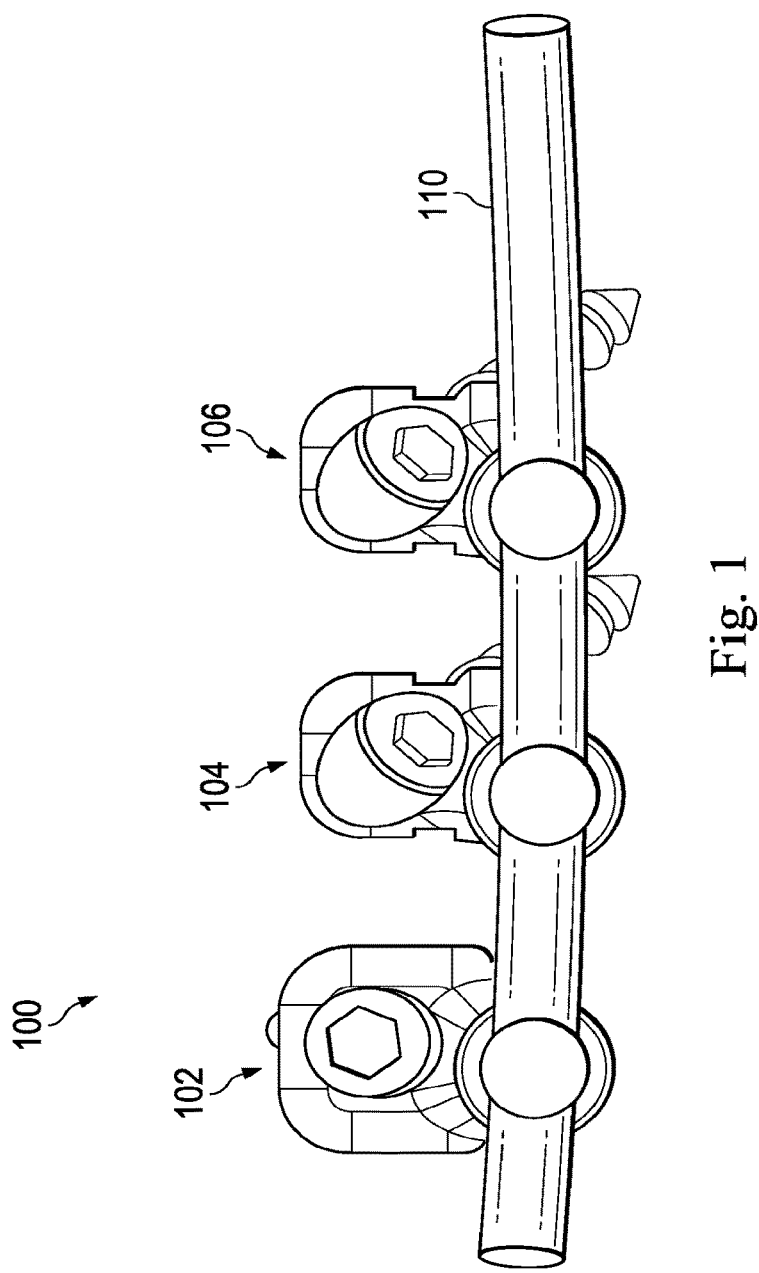
FIG. 1 is a top view of an exemplary posterior cervical stabilization system in accordance with various aspects of the disclosure.

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

FIG. 1 illustrates an exemplary posterior stabilization system in accordance with the disclosure. A posterior cervical stabilization system 100 may include two or more jigs or modular components 102, 104, 106 with a top loading rod 110. Although the illustrated embodiments show systems 100 have two and three modules, it should be appreciated that the systems contemplated by this disclosure may include any number of modules.

The modules 102, 104, 106 are oriented on the lateral masses with fixation with titanium screws into the bone of the lateral mass with an orientation outward about 20-40° and angulation rostrally about 20-40°. The modules 102, 104, 106 have a low profile and either lock to the interphase of the module or are held with a locking mechanism. The laterally held rod 110 can be polyaxial or non-polyaxial with its connection to the modules with a top loading nut.

As shown in FIG. 1, module 102 may be oriented medially about 10-15° and used with a $C_7$ or thoracic screw. Modules 104, 106 are the lateral mass components oriented laterally about 20-40° and rostrally about 20-40°.

Figure 2:
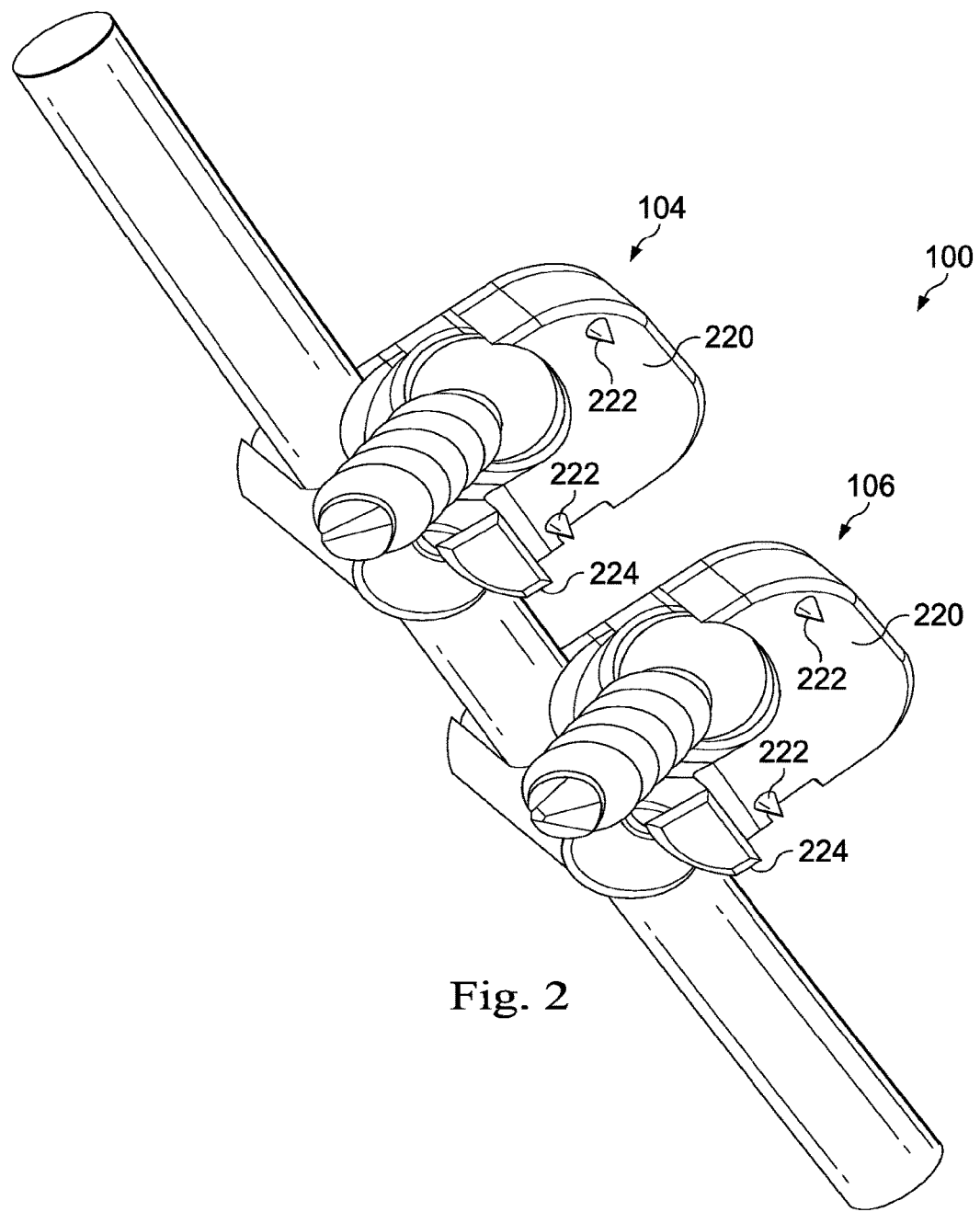
FIG. 2 is a bottom view of an exemplary posterior cervical stabilization system in accordance with various aspects of the disclosure.

Referring to FIG. 2, a bottom surface 220 of the modules 104, 106 may include one or more small spikes 222, or example, 1-2 mm extensions from the bottom surface. The spikes 222 can be used to temporarily hold the modules to a lateral mass bone prior to the creation of screw holes for receiving the screws. The bottom surface 220 of the modules 104, 106 may also include a lateral flange 224 oriented toward the lateral aspect of the lateral mass to help with centering the module 104, 106. Although not depicted in FIG. 2, module 102 may similarly include spikes and a lateral flange for holding and centering the module during a procedure.

Figure 3:
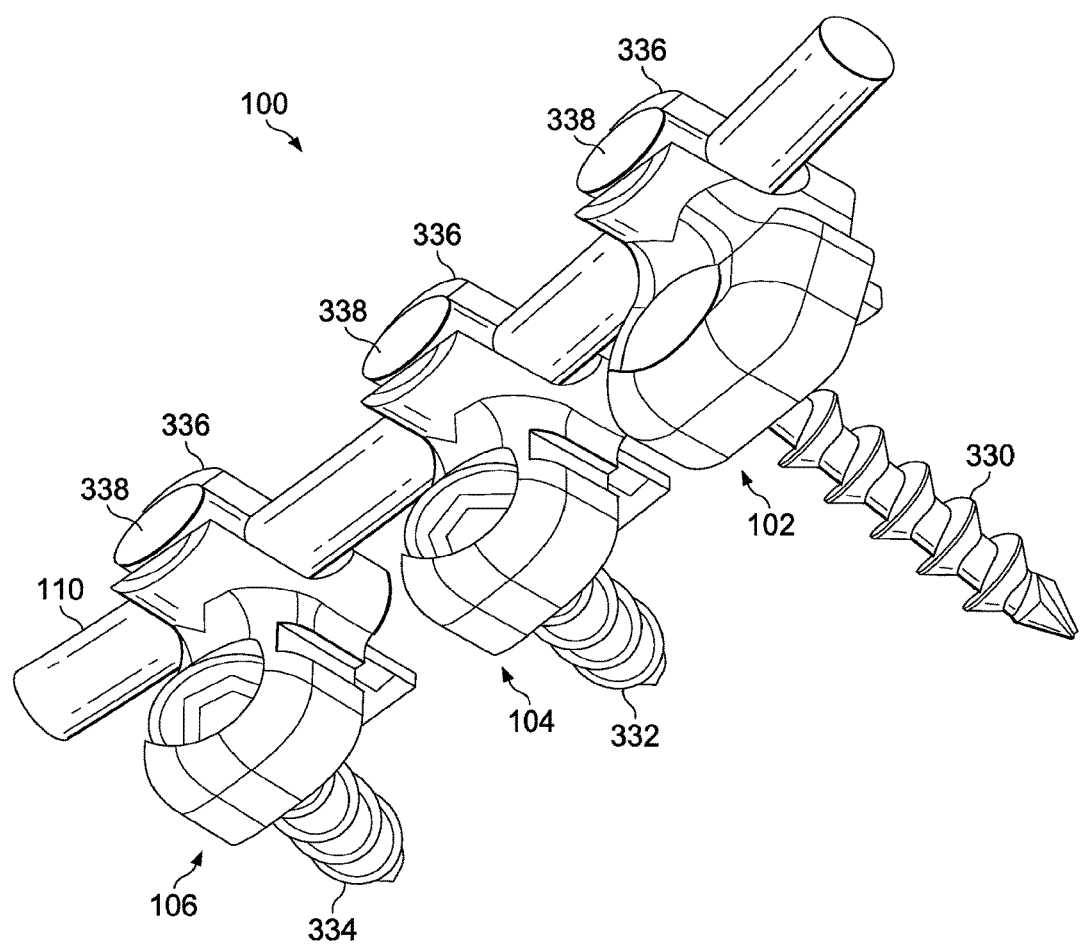
FIG. 3 is a lateral view of an exemplary posterior cervical stabilization system in accordance with various aspects of the disclosure.

Referring now to FIG. 3, the module 102 includes the $C_7$ or thoracic screw 330 oriented about 10-15° medially. The modules 104, 106 include the lateral mass screws 332, 334, which are oriented about 20-40° laterally and about 20-40° rostrally away from the spinal cord.

The modules 102, 104, 106 are individually oriented over the center of the lateral mass, and each includes a predrilled hole with appropriate lateral and rostral orientation. Accordingly, the modules 102, 104, 106 can be held and holes can be drilled, tapped, and the screws fixated and locked to the modules.

The rod 110 may be formed of titanium, polyethylene ketone (PEEK), carbon fiber, or other suitable composites that provide the desired characteristics of flexibility/stiffness, biocompatibility, imaging characteristic, and the like. The modules 102, 104, 106 include a top-loading polyaxial or non-polyaxial screw top 336 that receives the rod 110. The rod 110 can be secured to the modules with top loading nuts 338 that couple with the screw tops 336. It should be appreciated that other conventional securing mechanisms are contemplated by this disclosure.

Figure 4:
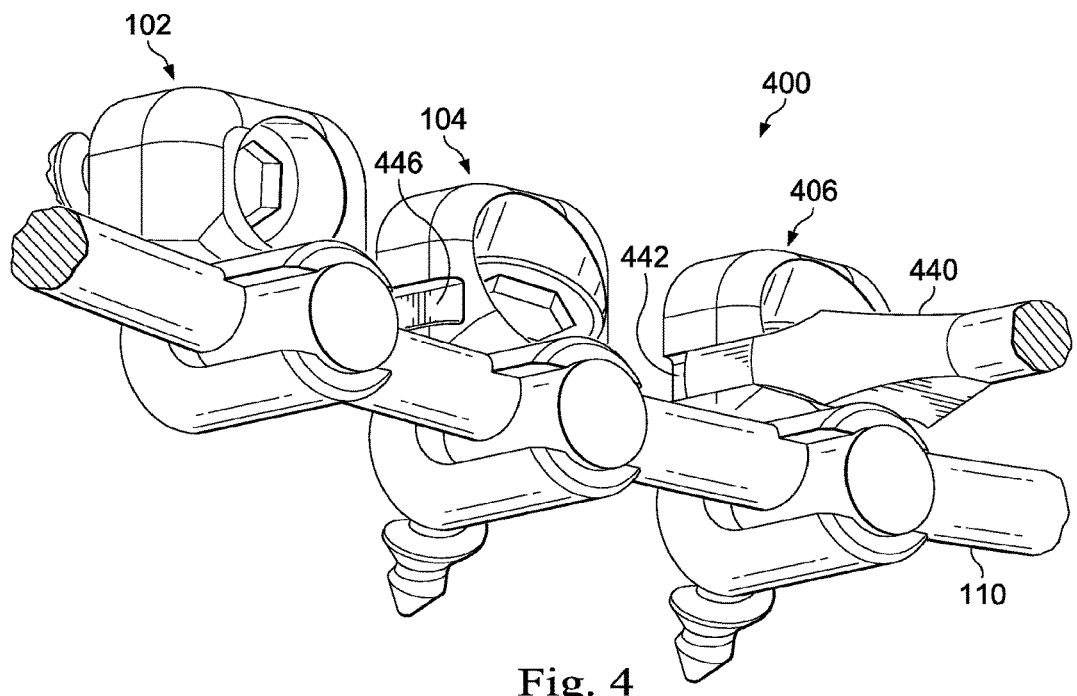
FIG. 4 is a top view of an exemplary posterior cervical stabilization system in accordance with various aspects of the disclosure.

FIG. 4 illustrates the stabilization system 350 during an exemplary implantation procedure. The system 350 includes a top-loading introducer fork device 352 that can straddle a module 354 and couple with the module via engagement with grooves 356 in the sides of the module 354. The fork device 352 can thus temporarily secure the positioning of the module during drilling and placement of the screws.

Figure 5:
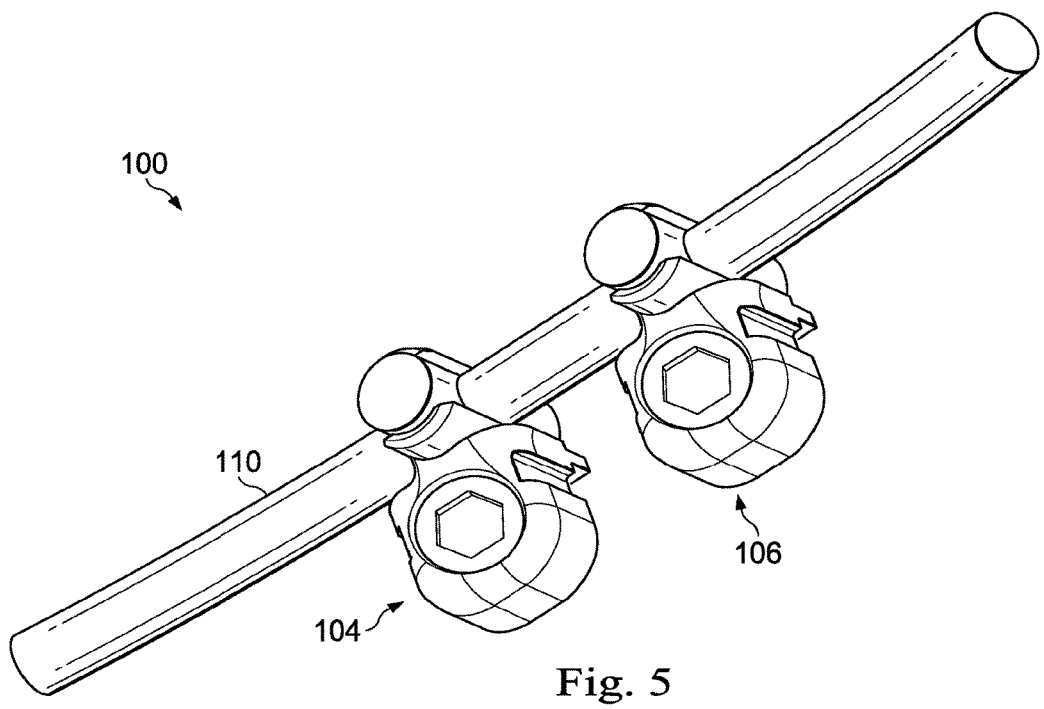
FIGS. 5-6 are alternate views of the exemplary system of FIG. 2.
Figure 6:
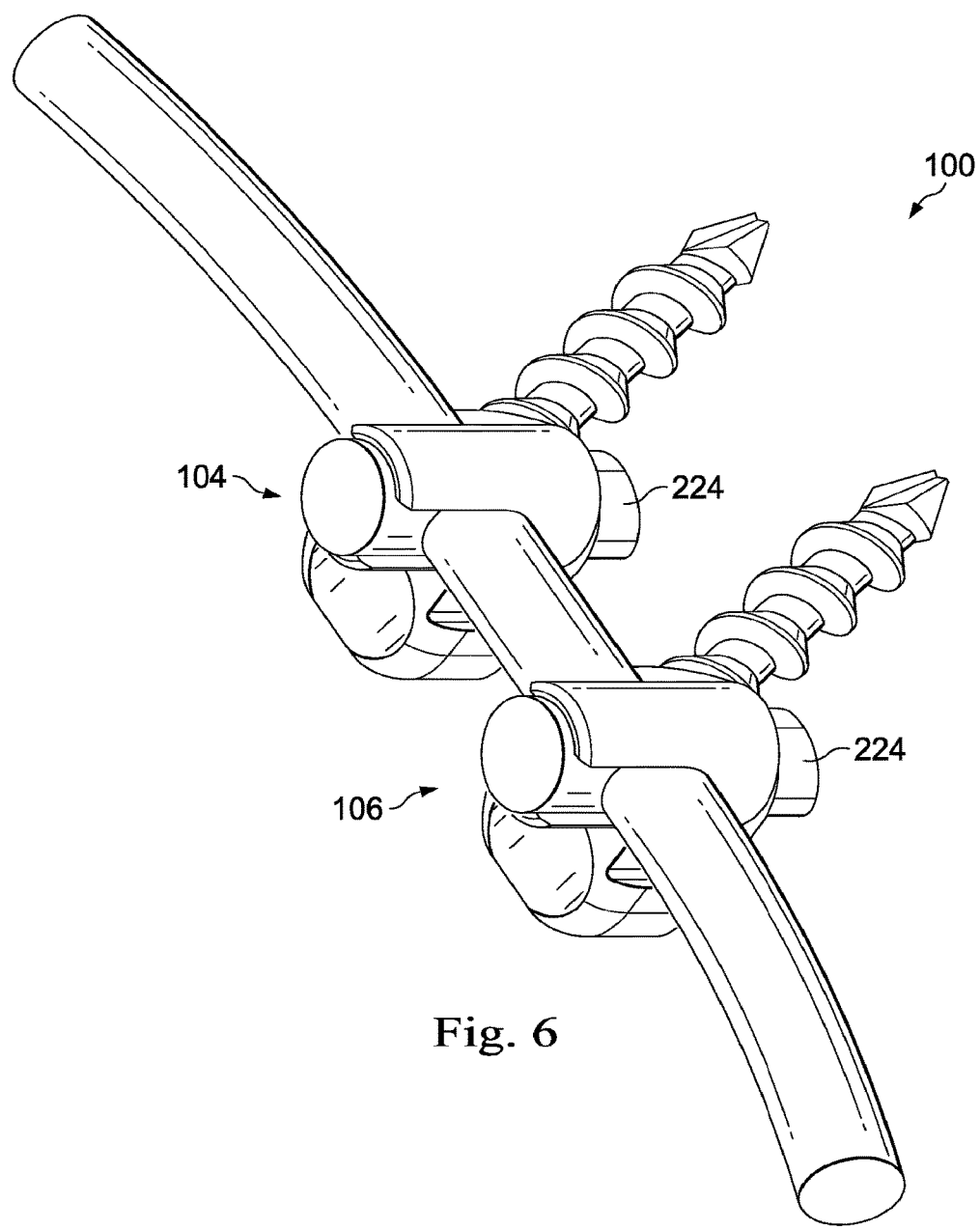
Figure 7:
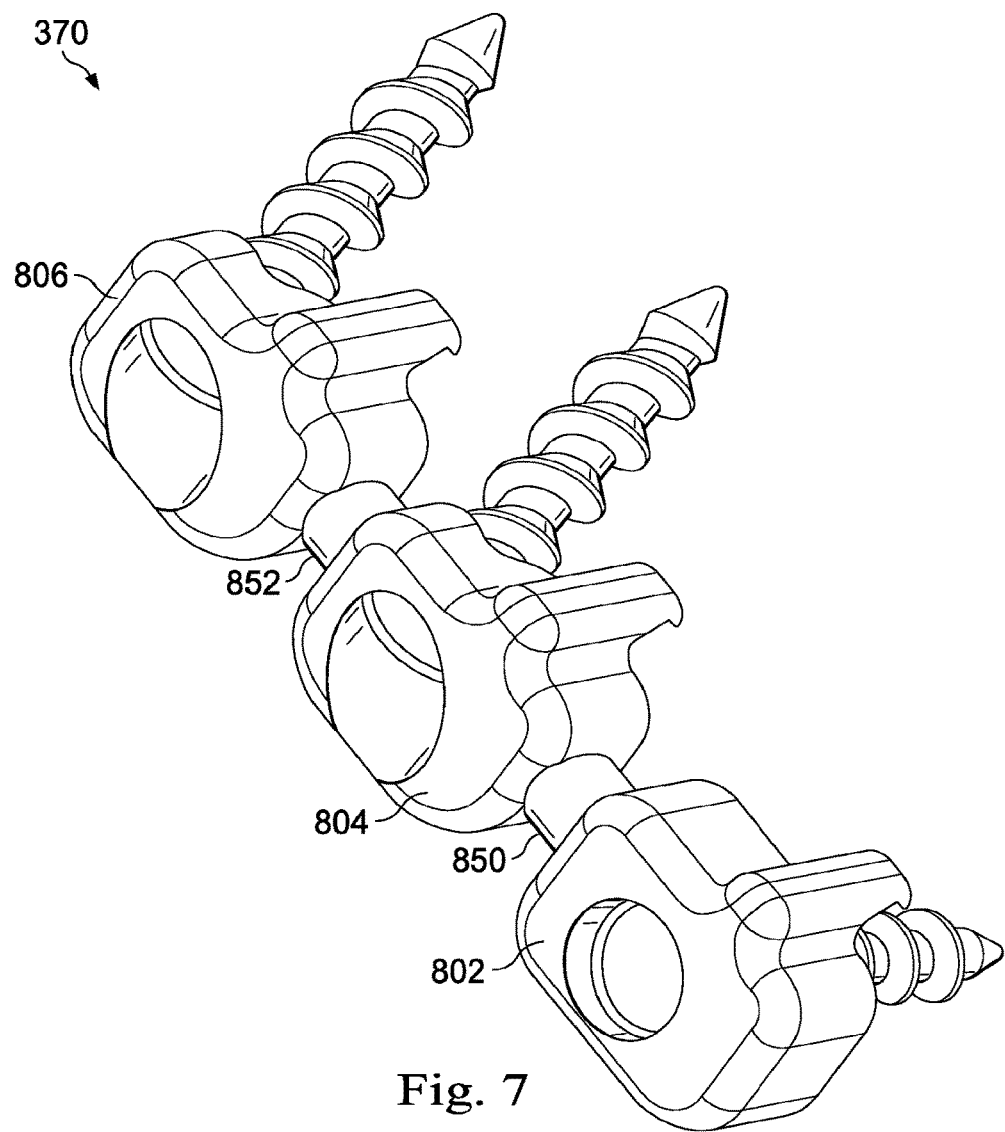
FIG. 7 is a top view of another exemplary posterior cervical stabilization system in accordance with various aspects of the disclosure.

FIGS. 5 and 6 illustrate different views of the system shown in FIG. 2 so that additional aspects and features of the disclosure can be appreciated. FIG. 7 illustrates an alternative stabilization system 370 where the modules 372, 374, 376 are fixedly coupled to one another via connecting elements 378, 380 rather than via a rod.

This posterior cervical stabilization system is better than other conventional system because this system is able to produce more reproducible screw angles, which promotes more safety.

FIGS. 8-13 illustrate another exemplary embodiment of a posterior cervical stabilization system, referenced herein by the numeral 400. The system includes a jig 402, a fastener 404 (FIG. 11) configured to anchor the jig 402 to a bone construct, a rod connector 406, and a set screw 408 (shown in FIGS. 12 and 17). In the embodiment shown, the system 400 is attached along a lamina of a cervical vertebra to provide an anchor for a rod 409 (shown in FIGS. 12 and 13) that is received in the rod connector 404. The illustrated vertebra represents a C2 segment and has a pedicle P and a lateral mass LM. As illustrated, the jig 400 extends across the top of the pedicle P and engages the lateral mass LM. The fastener 404 (shown in dash in FIG. 11) extends laterally away from the spinal midline to engage bone within the lateral mass LM. In the illustrated embodiment, the fastener trajectory is substantially transverse to the pedicle longitudinal axis LP.

Figure 11:
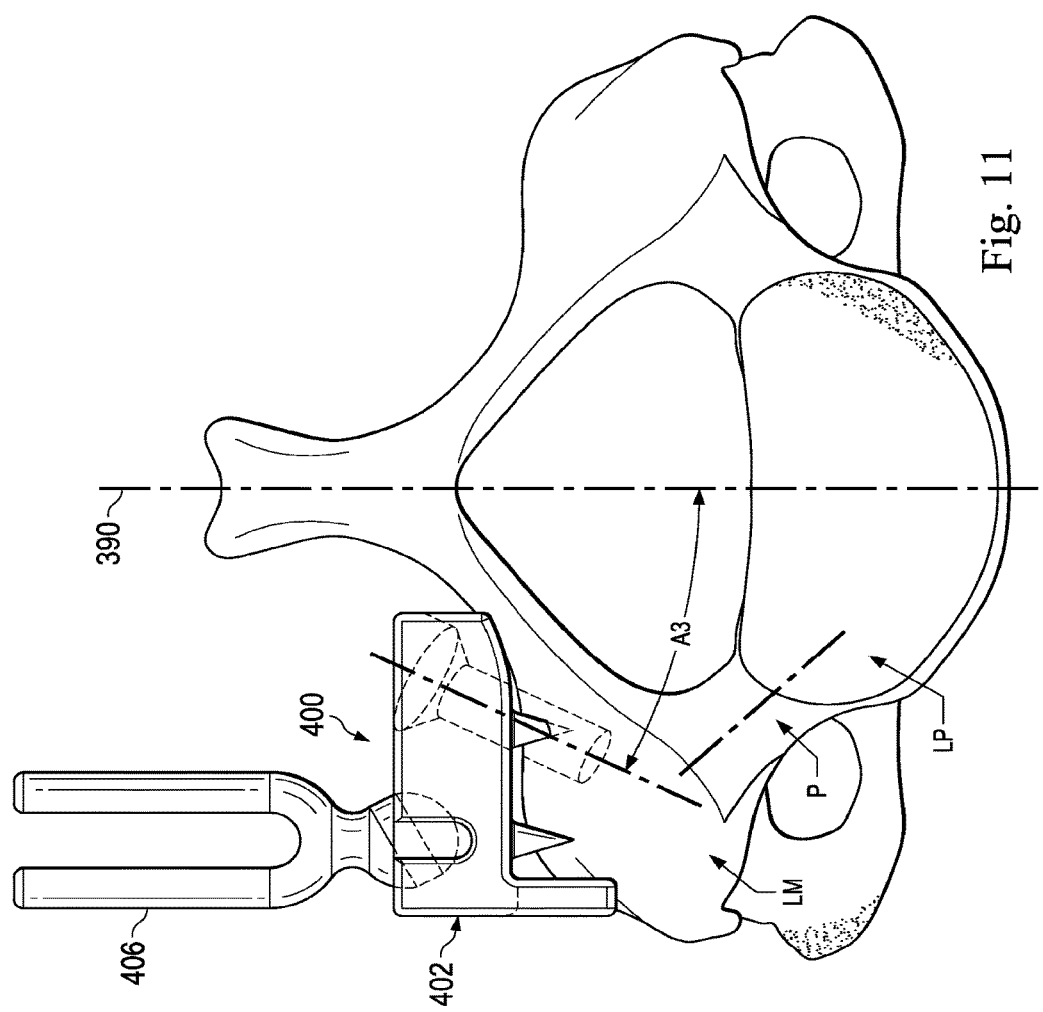
FIG. 11 illustrates a side view of the exemplary posterior cervical stabilization system of FIG. 8 in place on a vertebra showing hidden lines representing features of the system in accordance with various aspects of the disclosure.
Figure 12:
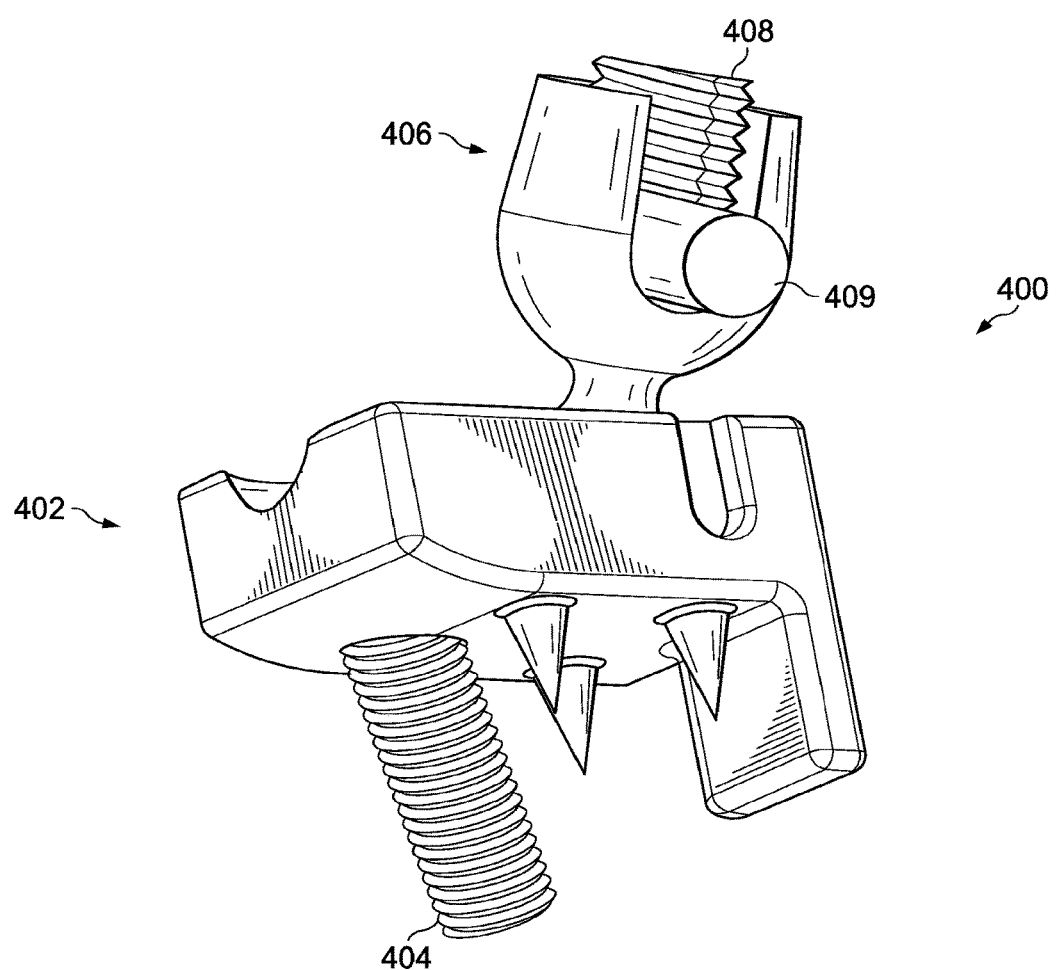
FIG. 12 illustrates an isometric view of an exemplary posterior cervical stabilization system in accordance with various aspects of the disclosure.
Figure 13:
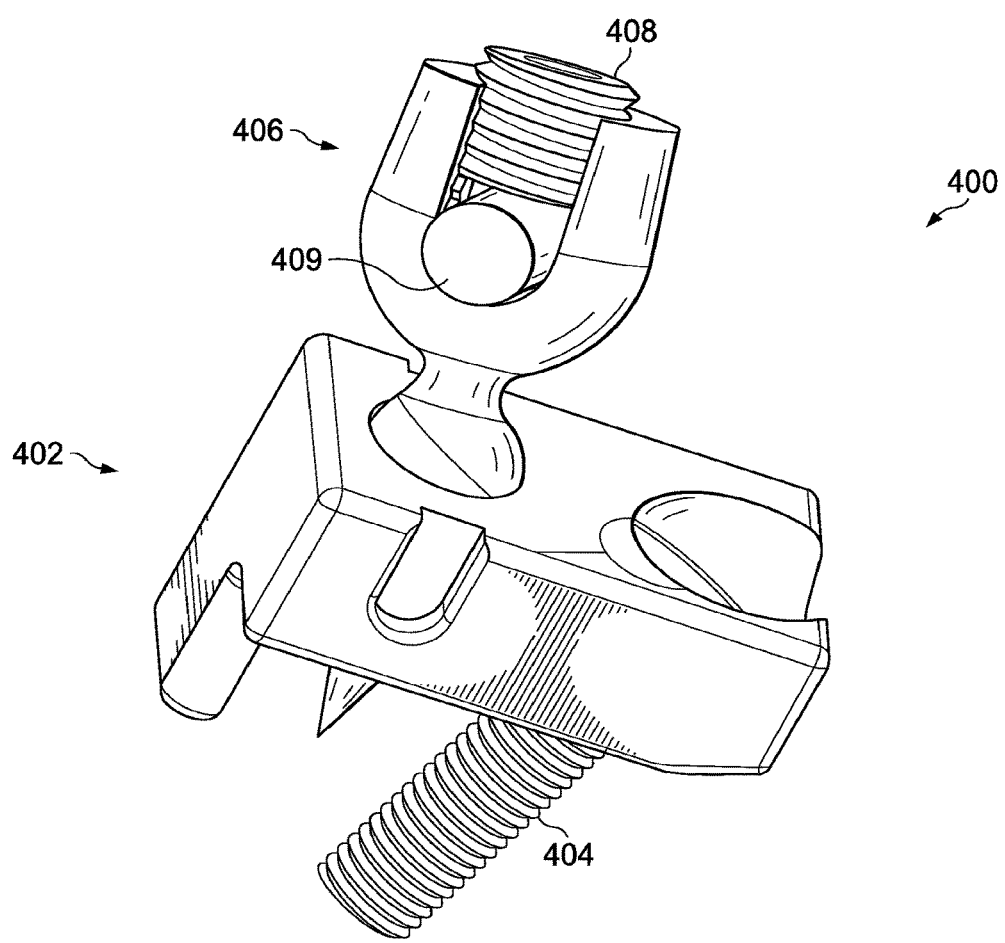
FIG. 13 illustrates an isometric view of the exemplary posterior cervical stabilization system of FIG. 12 in accordance with various aspects of the disclosure.

FIGS. 12 and 13 show the system independent of the bone structure itself in an assembled condition with FIG. 12 showing an internally facing side or bottom side, and FIG. 13 showing the outwardly facing side or top side. Although the rod connector 406 differs slightly in appearance between FIGS. 8-11 and 12-13, for ease of understanding, the same reference numbers are used. FIGS. 14A-14E show the jig 402 in greater detail. The jig 402 is formed, in this embodiment, of a solid rigid material and is formed substantially as a block or body having a number of protrusions extending therefrom. The jig 402 includes an outwardly facing or top side 418, an inwardly facing side or bottom side 420, two side edges 422a, 422b, a medial end 424 configured to be medially disposed when implanted on a vertebra, and a lateral end 426 configured to be laterally disposed when implanted on a vertebra as shown in FIGS. 8-11. Since some embodiments of the jig 402 are configured to be implanted along the cervical vertebrae, the jig is sized to fit to the vertebra and to be relatively discreet after implantation. Therefore, some embodiments of the jig 402 have a length from the medial end 424 to the lateral end 426 in the range of about 10-22 mm, a width from the side edge 422a to side edge 422b in the range of about 6-15 mm, and a height between the flat outwardly facing surface 418 to the flat inwardly facing surface 420 of about 4-10 mm. In other embodiments, the length is in the range of about 14-18 mm, the width is in the range of about 8-12 mm, and the height is in the range of about 5-7 mm. In one embodiment, the length is 16 mm, the width is 10 mm, and the height is 6 mm. However, other embodiments have dimensions greater and smaller than those identified herein.

The outwardly facing side 418 is substantially flat and includes a fastener opening 428 leading to a through bore 430 for receiving the fastener 404. In the exemplary embodiment shown, the outwardly facing side includes an opening 432 to a rod connector attachment feature 433 for affixing the rod connector 406. In this example, as will be described further below, the bore 430 is formed at an oblique angle through the jig 402. As such, the fastener opening 428 is oval shaped, and the fastener opening 428 intersects with the medial end 424. In one embodiment, the opening 428 has a diameter measured along the bore 430 of about 6.4 mm, although other sizes, larger and smaller are also contemplated.

Each side edge 422a, 422b includes an instrument engaging feature 434 sized and arranged to interface with an introducer instrument (described below). In this embodiment, in order to reduce the likelihood of slippage along the jig 402, the instrument engaging feature 434 is a slot-like indentation extending along each side edge 422a, 422b from the outwardly facing side 418 toward the inwardly facing side 420. The instrument engaging feature 434 has open end at the outwardly facing side 418 and a closed end 436. As such, the instrument is less likely to slip even if the surgeon applies loading toward the bone construct by pressing the internally facing side 420 against a vertebra. In the example shown, the instrument engaging features 434 are disposed closer to the lateral end 426 than the medial end 424. This places the instrument engaging features 434 closer in proximity to protruding features on the inwardly facing side 420 and may enable easy access to the fastener opening 428 for the placement of the fastener 404. Here, they are aligned with protruding features and the rod connector feature opening 432. However, other embodiments have the instrument engaging features 434 disposed centrally or even toward the medial end 424.

Since the embodiment of the jig 402 shown in FIGS. 12-14 is configured and arranged for implantation on the cervical vertebra, some embodiments are minimally sized in order to make the implant as discrete as possible on the patient's neck. In the embodiment shown, and as described above, the fastener opening 428 is sized and disposed to intersect the medial end 424. As such, the bore 430 also intersects the lateral end, providing a recessed arc 438 in the lateral end.

The bottom or inwardly facing side 420 includes a relatively planar surface portion 446 and a relatively tapered surface portion or curved surface portion 448. The curved surface portion 448 is disposed toward the medial end 424 of the jig 402 and curves from the flat surface portion to the intersection of the inwardly facing side 420 and the medial end 424. In some embodiments the radius of curvature is within the range of about 5-20 mm. In other embodiments, the radius of curvature is within a range of about 8-12 mm. Further, the curved surface portion intersects the planar surface portion at a location about 50-80% of the distance from the lateral end 426. The curved surface portion 448 is a bone abutting portion located and shaped to abut against the lamina of the vertebra.

A plurality of protruding features extends from the planar surface portion 446 and is configured to engage and help locate the jig 402 on the vertebra. In the embodiment shown, the protruding features include one or more penetrating features 450 and one or more lateral bone outriggers 452. The embodiment in FIGS. 14A-14E includes three penetrating features 450 and a single lateral bone outrigger 452. However, other numbers of features could be used to achieve desired functionality. The penetrating features 450 in this embodiment are formed as conical spikes that extend to a sharp point. These are configured to engage against and penetrate the bone structure when the jig 402 is in place against the lamina and/or lateral mass of the vertebra. In the embodiment shown, at least two of the penetrating features are disposed on opposite sides (but extending from the inwardly facing side 420) of the attachment feature opening 432, as can be seen in the bottom view of the jig 104 in FIGS. 14A-14E. In this embodiment, the penetrating features 450 are located within the range of about 2-13 mm from the lateral end 426. In some embodiments, the penetrating features 450 disposed on opposing sides of the attachment feature and are about 4-7 mm from the lateral end 426. In addition, in some embodiments, at least two penetrating features 450 are disposed equal distances from and on opposing sides of a centerline through the jig 402 extending from the medial end 424 to the lateral end 426. In this embodiment, the penetrating features 450 have a height that is less than a height of the lateral bone outrigger 452. For example, the penetration features 450 may have a height in the range of about 50-75% of the height of the lateral bone outrigger 452. In one embodiment, the penetrating features have a height about 3.5 mm from the planar surface portion 446.

Figure 8:
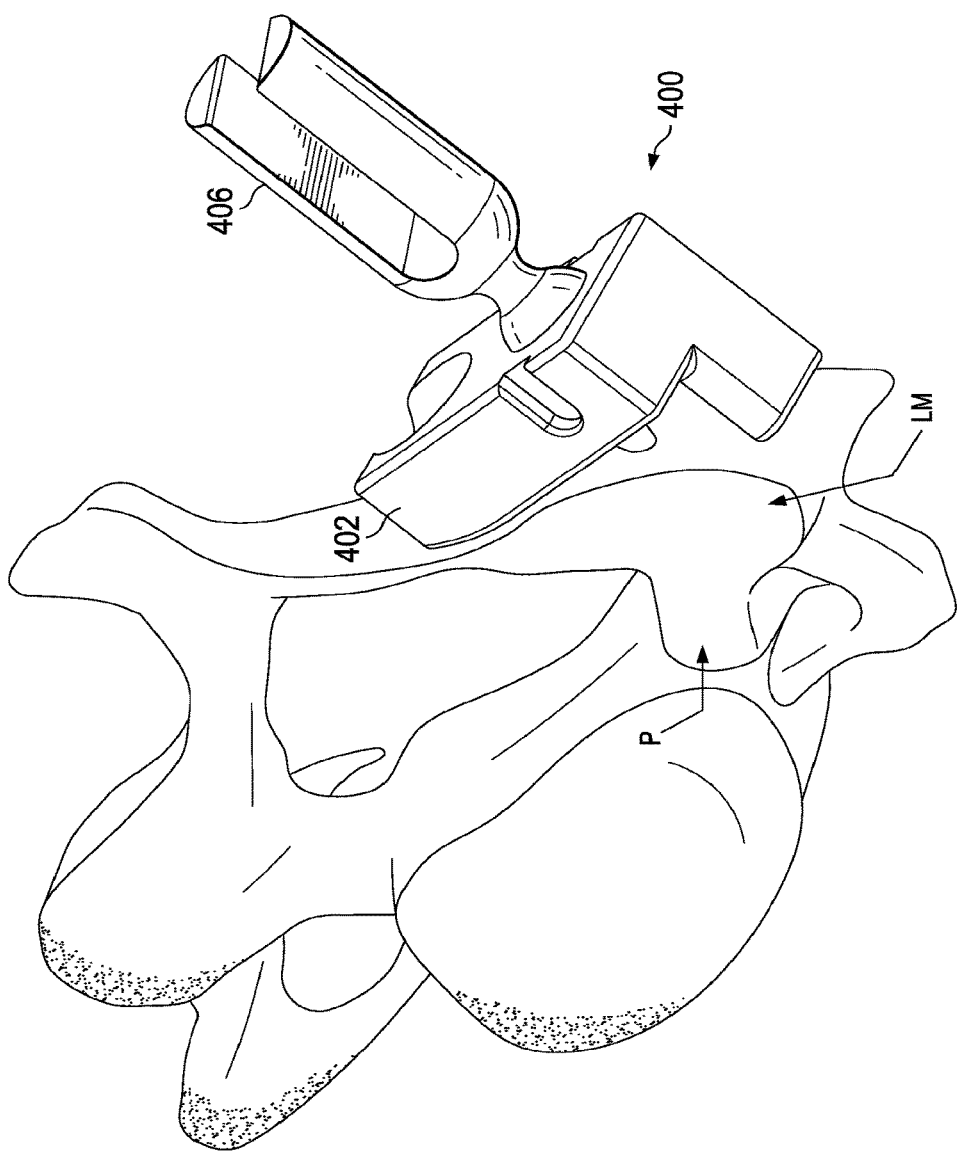
FIG. 8 illustrates a perspective view of another exemplary posterior cervical stabilization system in place on a vertebra in accordance with various aspects of the disclosure.
Figure 9:
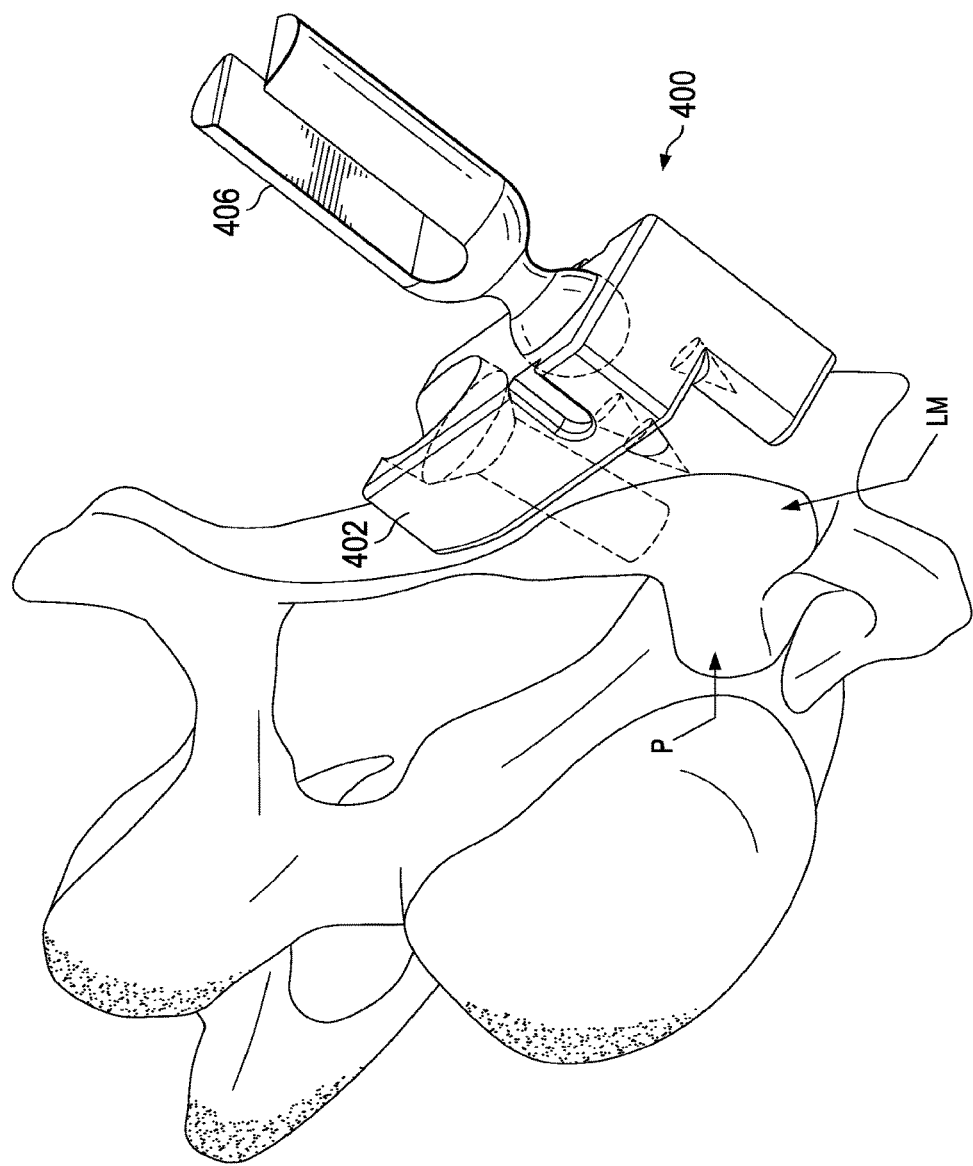
FIG. 9 illustrates a perspective view of the exemplary posterior cervical stabilization system of FIG. 8 in place on a vertebra showing hidden lines representing features of the system in accordance with various aspects of the disclosure.
Figure 10:
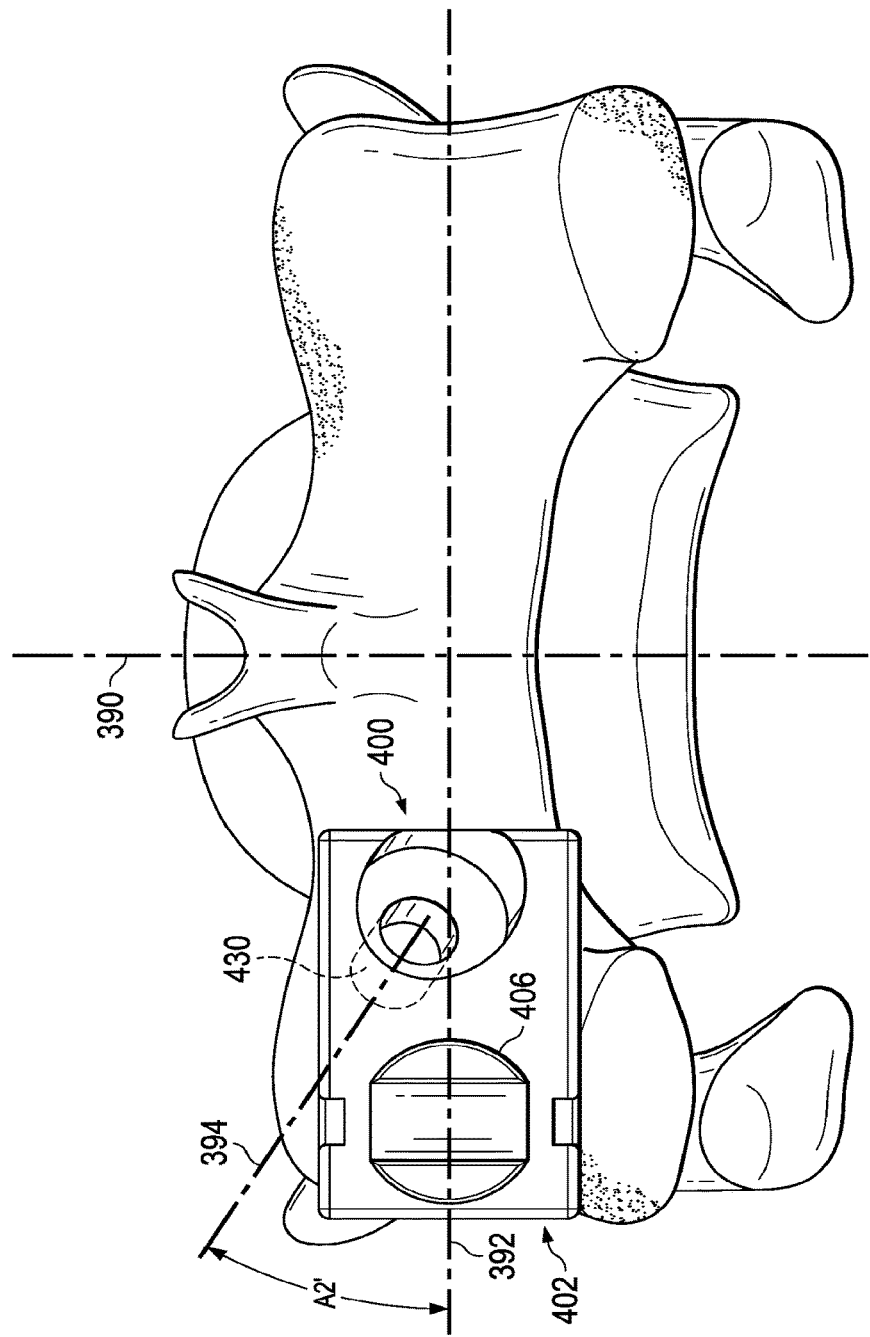
FIG. 10 illustrates a top view of the exemplary posterior cervical stabilization system of FIG. 8 in place on a vertebra in accordance with various aspects of the disclosure.

The lateral bone outrigger 452 is configured to abut against bone structure as shown in FIG. 8-11. In this embodiment, the lateral bone outrigger 452 is configured to rest against the exterior surface of the lateral mass and includes a smooth abutting surface and is devoid of a sharp point or edge. The lateral bone outrigger 452 is disposed proximate the lateral end 426, and in the embodiment shown, is flush with the lateral end 426. It has a bone-abutting surface 454 disposed on a medial side or along a top medial/medial side that is configured to rest against the bone to provide lateral support to the jig 402 when the jig is implanted. Because of the curvature of the lateral mass (as seen in FIG. 8), the bone-abutting portion 454 is in part on the bottom and/or medial side of the lateral bone outrigger 452. In some embodiments, it is formed by a chamfer or round connecting the end and the medial sides of the lateral bone outrigger 452. The lateral bone outrigger 452 also has a height greater than that of the penetrating features 450 so that it can engage the perimeter of the lateral mass even while the jig 404 does not follow the curvature of the lamina and lateral mass, as can be seen in FIG. 11. For example, the lateral bone outrigger 452 may have a height in the range of about 4-8 mm, and more preferably, about 5-6 mm. However, other heights, both larger and smaller are contemplated. Because of its height and arrangement, the lateral bone outrigger 452 and inwardly facing surface may create a gap between the bone and the jig 402. As such, when properly implanted the jig 404 may operate as a simple beam with the jig abutting against the bone at the medial portion and at the lateral portion, such that loading against the bone occurs at the medial portion and at the lateral portion, but much less so between these portions where the penetration features are disposed. The fastener may then apply opposite loading in the region between the abutting portions.

The embodiment shown in FIGS. 14A-14E includes the lateral bone outrigger 452 as a wall extending from the planar surface portion, substantially flush with the lateral end 426, and extending from one of the side edges 422a, 422b toward the other. However, as can be seen, in the exemplary embodiment shown, the lateral bone outrigger 452 does not extend across the width and extends only just beyond the midline.

The bore 430 is disposed at an angle and extends from the outwardly facing surface 418 to the inwardly facing surface 420. It has a longitudinal axis and is sized and configured to receive the fastener 404 and direct the fastener 404 into the lateral mass of the vertebra. Accordingly, instead of being angled toward the pedicle, as do some devices, the bore 430 is disposed so that the angle directs the fastener 404 in a direction either somewhat perpendicular to or oblique to the pedicle. As such, the bore 430 extends in the direction of the lateral bone outrigger 452. The bore position may be determined by taking into account three angles: A1, A2, and A3, each labeled in FIGS. 14A-14E. In the embodiment shown, a cross-section through the bore 430 shows the bore 430 is angled at an angle A1 within a range of about 20-55 degrees for example. In some embodiments, the angle A1 is within a range of about 25-45 degrees, and in yet other embodiments, the angle A1 is within a range of about 26-41 degrees. Some embodiments have an angle A1 about 27 degrees, while other embodiments have an angle A1 of about 40 degrees.

In addition, in the embodiment shown the bore 430 is angled relative to the side 422a at an angle A2 within a range of about 20-55 degrees for example. In some embodiments, the angle A2 is within a range of about 25-45 degrees, and in yet other embodiments, the angle A2 is within a range of about 26-41 degrees. Some embodiments have an angle A2 about 30 degrees, while other embodiments have an angle A2 of about 40 degrees. In some embodiments, the angles A2 and A1 are within about 15 degrees of each other. In other embodiments, the angles A2 and A1 are within about 10 degrees of each other. In the embodiment shown, the angles A2 and A1 are within about 5 degrees of each other. In some embodiments, the bone may have an orientation of about 20-40° laterally (shown by angle A2, away from the spinal cord) and rostrally about 20-40° (shown by angle A1, toward the head).

These angles also may be described with reference to the vertebra as shown in reference to FIGS. 10 and 11. FIG. 10 shows the sagittal plane 390 and the axial plane 392. FIG. 10 also shows a direction or longitudinal axis 394 of the bore 430, which substantially corresponds to that of the implanted fastener 404 in FIG. 11. As can be seen, the longitudinal direction of the bore 430 and fastener 404 is angled at the angle A2 from the axial plane 392, extending away from the sagittal plane 390 within a range of about 20-55 degrees. In some embodiments, the angle A2 is within a range of about 25-45 degrees, and in yet other embodiments, the angle A2 is within a range of about 26-41 degrees.

Figure 14A:
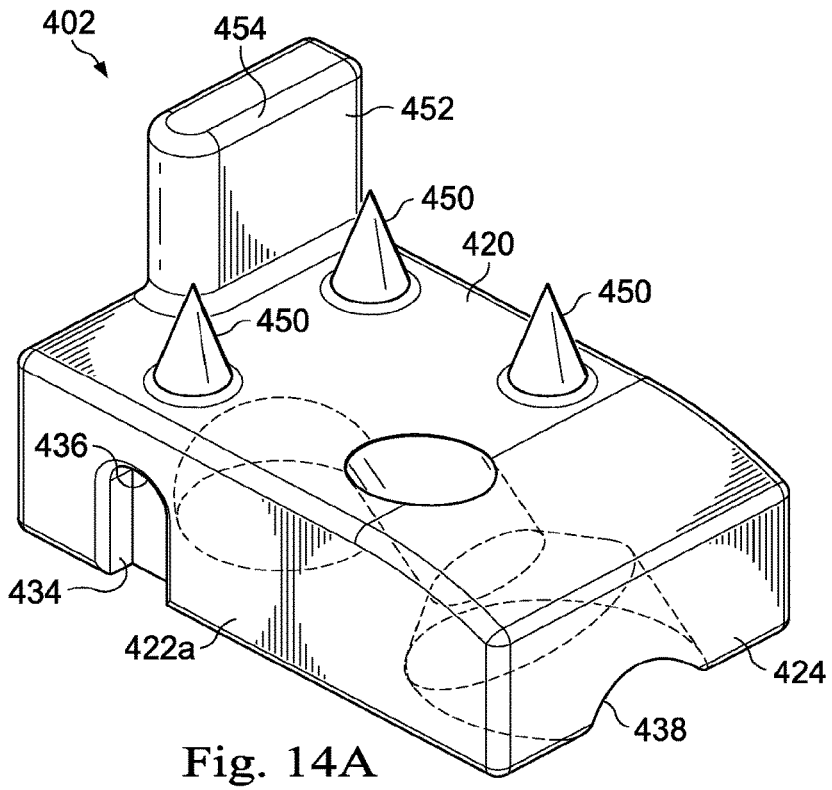
FIGS. 14A-14E illustrate views of an exemplary jig of the posterior cervical stabilization system of FIG. 12 in accordance with various aspects of the disclosure.
Figure 14B:
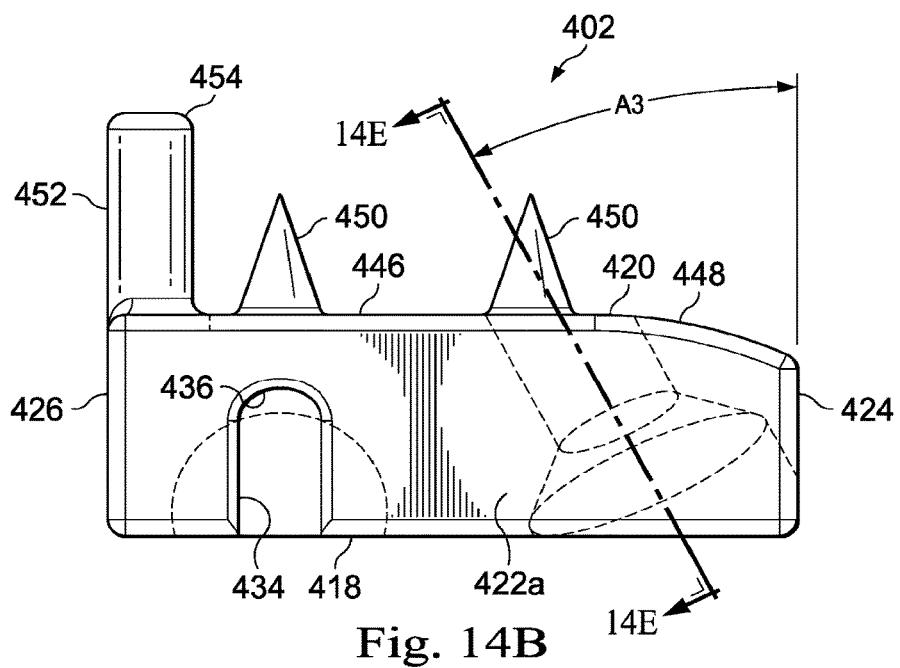
Figure 14C:
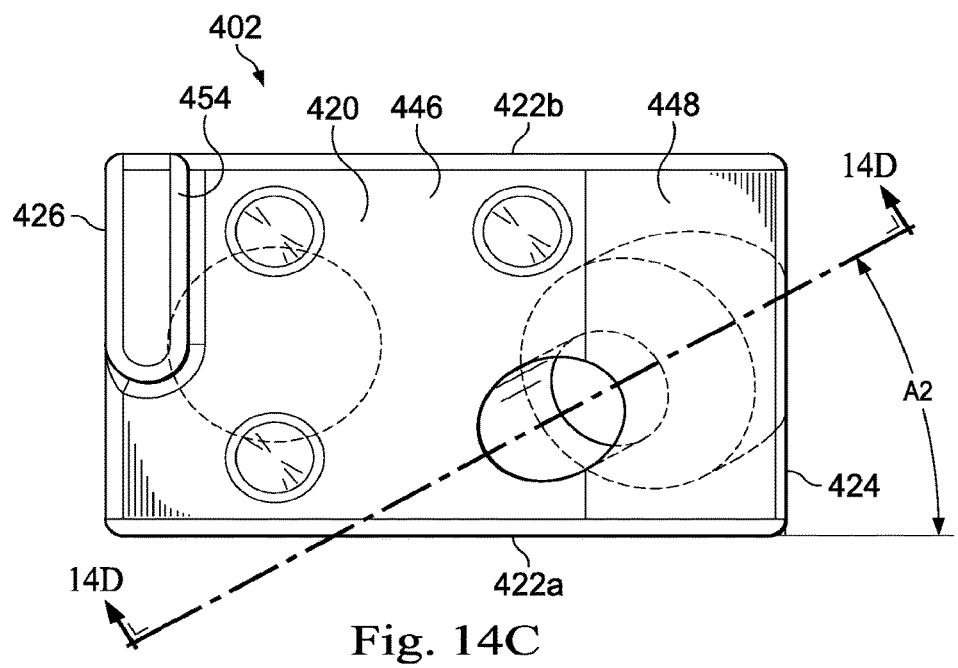
Figure 14D:
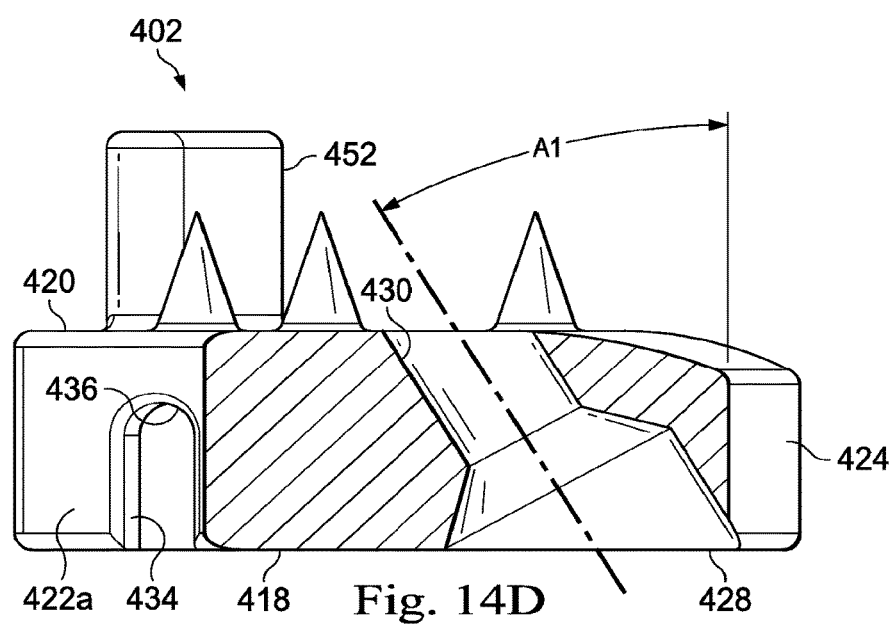
Figure 14E:
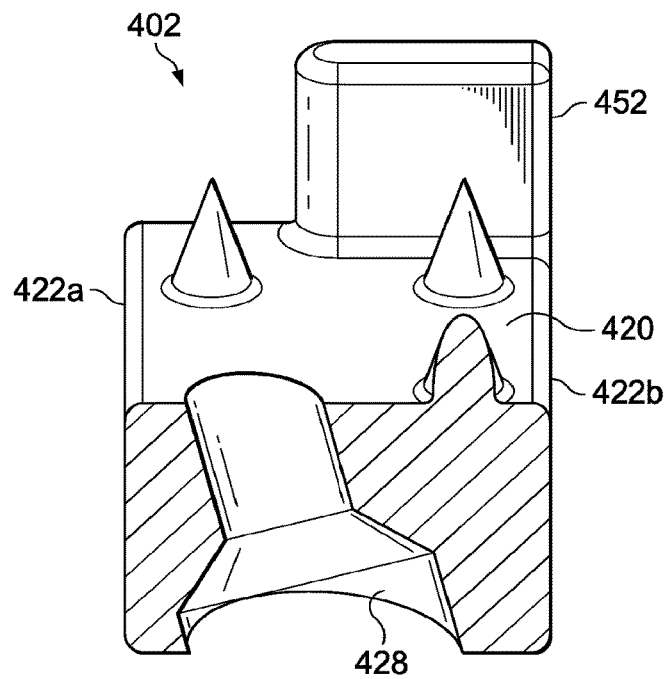

FIG. 11 shows the angle of the bore 430 and fastener 404 looking into the axial plane 392. As can be seen, the angle of the bore 430 and fastener 404 in this plane are within the range of a range of about 20-55 degrees. In some embodiments, the angle A3 is within a range of about 25-45 degrees, and in yet other embodiments, the angle A3 is within a range of about 26-41 degrees. In one embodiment, the angle A3 is 27 degrees. Angle A3 may also be measured from the medial side as shown in FIG. 14B. In addition, the rod connector 406 is disposed further from the axial plane 390 than the fastener 404, and the fastener extends into the lateral mass and is angled in a direction nearly transverse to the direction of the pedicle.

In the example shown the bore 430 is formed as a countersink bore so that the head of the fastener 404 may recess within the bore, reducing the chance of tissue trauma and providing an overall smoother profile. In some embodiments the bore 430 has a diameter between about 3-4 mm sized to fit a fastener that is suitable for engaging the lateral mass without breaking out of the lateral mass. Some embodiments have a square counterbore instead of a taper counterbore.

The opening 432 to the attachment feature 433 is formed on the outwardly facing surface and is configured to receive and engage the rod connector 406. The attachment feature 433 comprises a concave or spherical depression. In this example, the depression is disposed centrally along the centerline of the jig 402. It is configured as a spherical depression having a maximum inner diameter greater than the diameter of the opening 432 of the attachment feature 433. Accordingly, a lip is defined at the outwardly facing surface that mechanically prevents removal of a spherically shaped ball. In this example, the opening of the attachment feature 433 has a diameter of about 4.5-5.5 mm, although other sizes are contemplated. In one embodiment, the opening 432 has a diameter of about 4.8 mm and the diameter of the attachment feature 433 is 5.0 mm. The center of the spherical depression may be spaced from the outer surface 418 by a distance in the range of about 0.5-1 mm, although other distances are contemplated.

It's worth noting that some embodiments include a right implant and a left implant for use on the right or left sides of the vertebra. These may be mirror images of each other.

Figure 15:
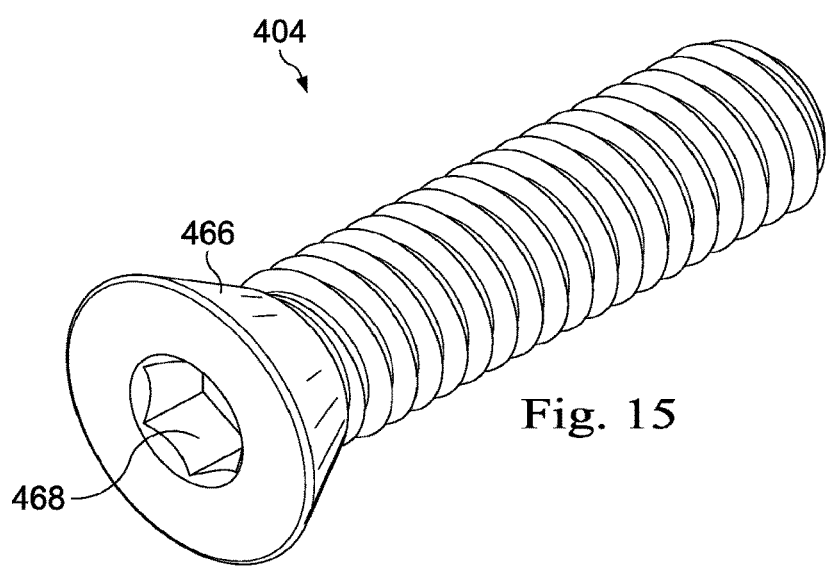
FIG. 15 illustrates an isometric view of an exemplary fastener of the posterior cervical stabilization system of FIG. 12 in accordance with various aspects of the disclosure.

FIG. 15 shows the fastener 404 in greater detail. In this embodiment, the fastener 404 is configured to perch within the lateral mass of the cervical vertebra. Therefore, the fastener in the embodiment shown as a thread length of about 12 mm and a total length of about 14 mm. Accordingly, the fastener 404 may project further from the inwardly facing surface than the penetrating features 450 when measured perpendicular from the inwardly facing surface as shown in FIG. 11, while the lateral bone outrigger 452 may project further from the inwardly facing surface than the fastener 404. As can be seen, the fastener 404 may include a tapered head 466 and a hex tool engaging recess 468. In addition, the fastener 404 may have a cylindrical leading end. Although the fastener 404 is shown as a bolt, other embodiments include a fastener formed as a screw, a nail, a staple, or other fastener.

Figure 16A:
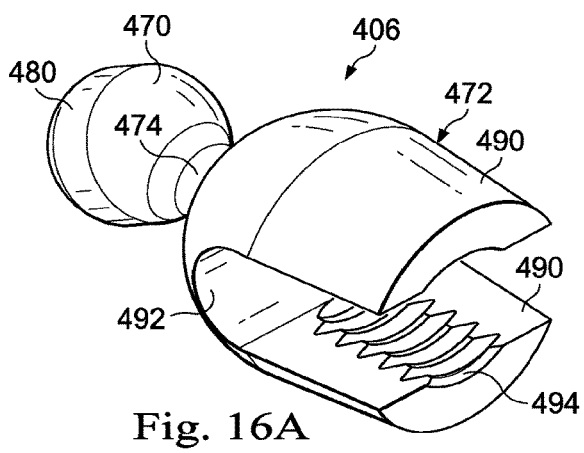
FIGS. 16A-16C illustrate views of an exemplary receiver of the posterior cervical stabilization system of FIG. 12 in accordance with various aspects of the disclosure.
Figure 16B:
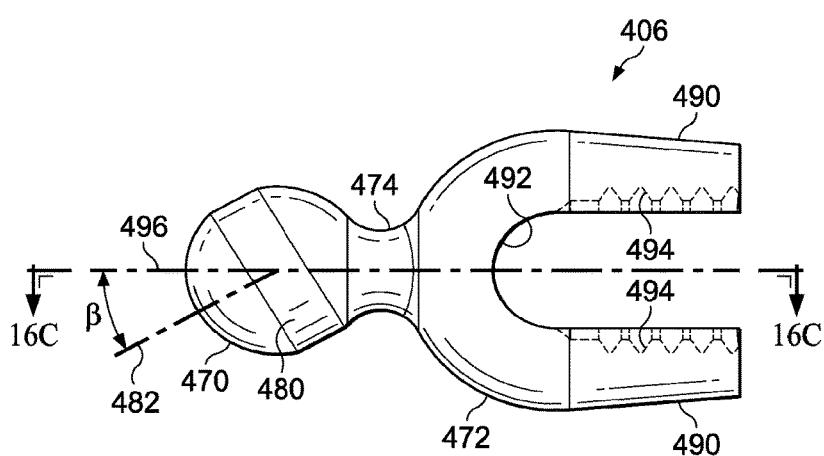
Figure 16C:
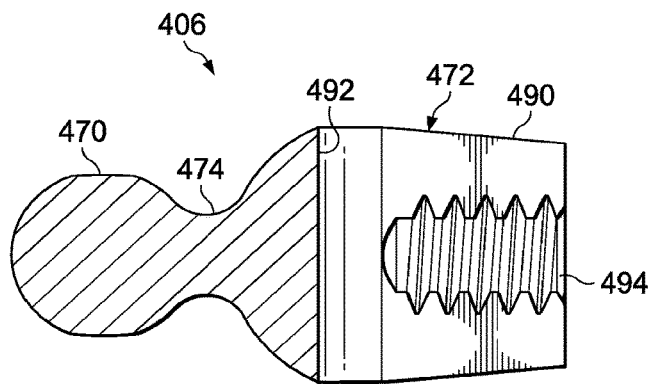
Figure 18A:
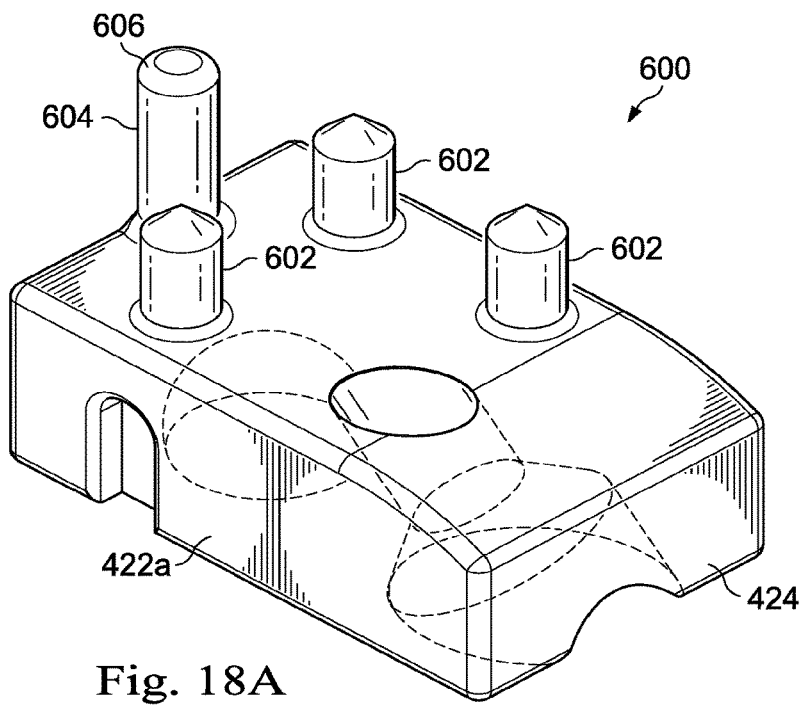
Figure 18B:
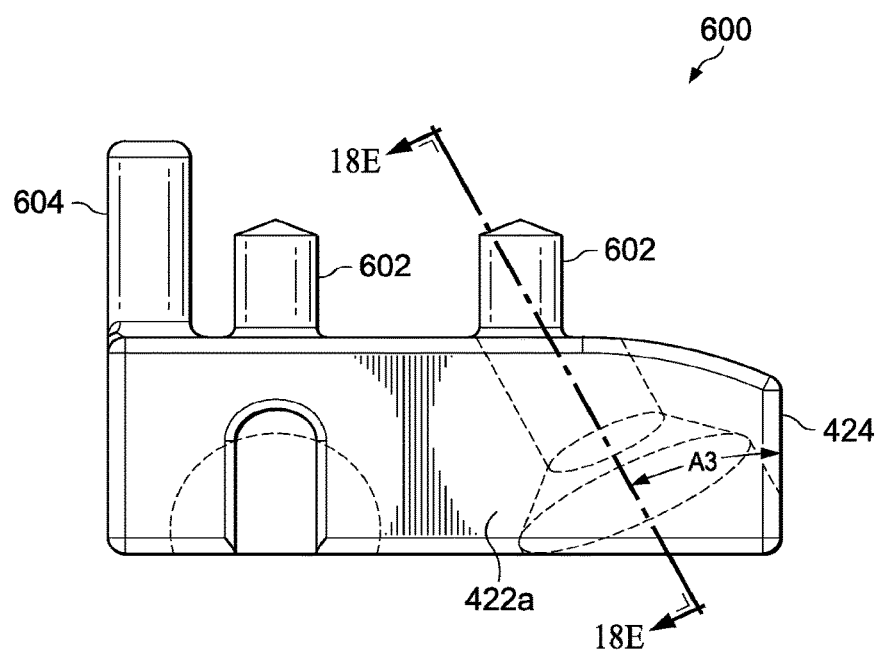
Figure 19A:
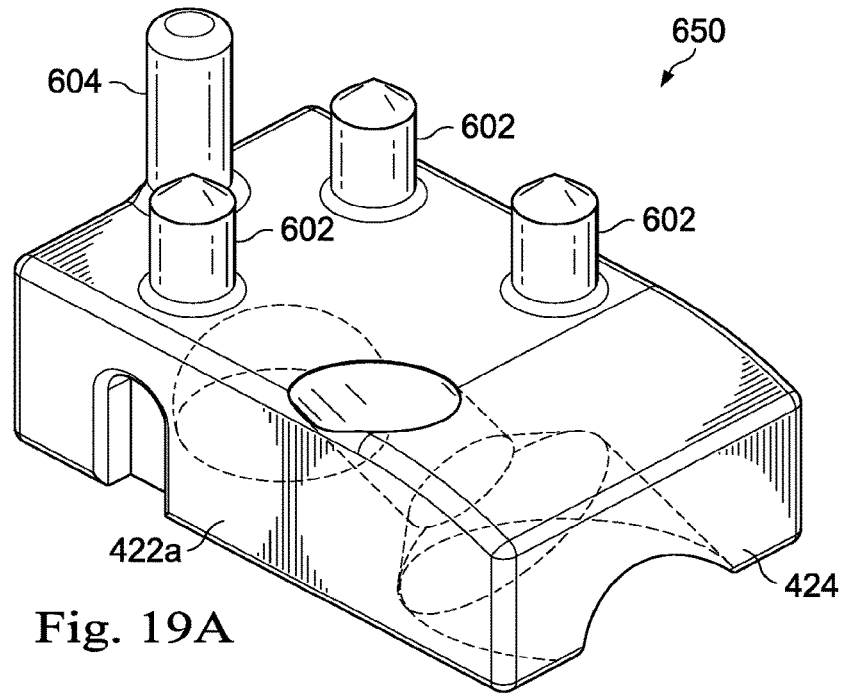
FIGS. 19A-19D illustrates views of an exemplary jig of the posterior cervical stabilization system in accordance with various aspects of the disclosure.
Figure 19B:
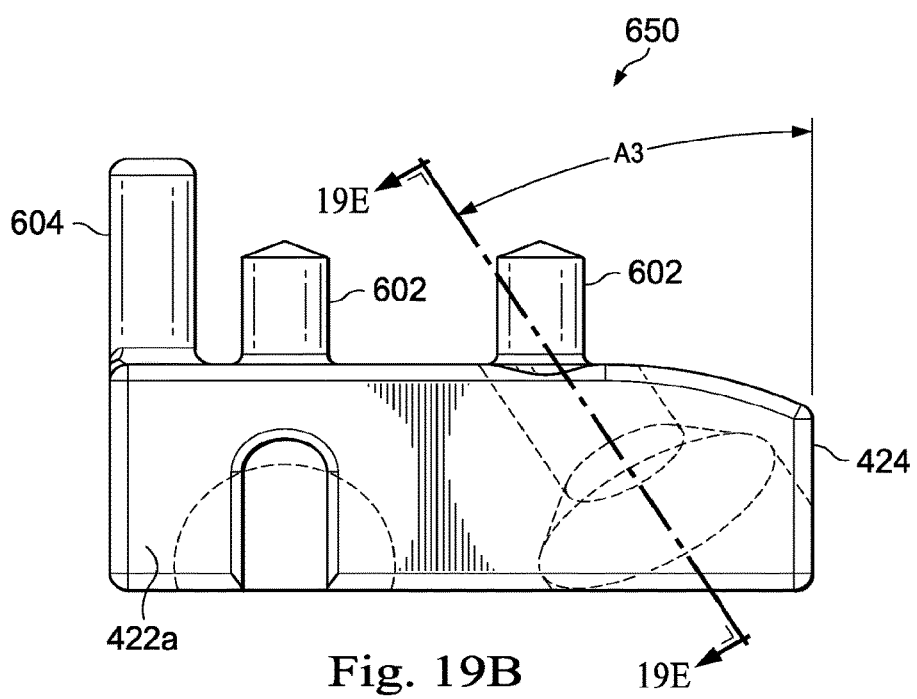
Figure 19C:
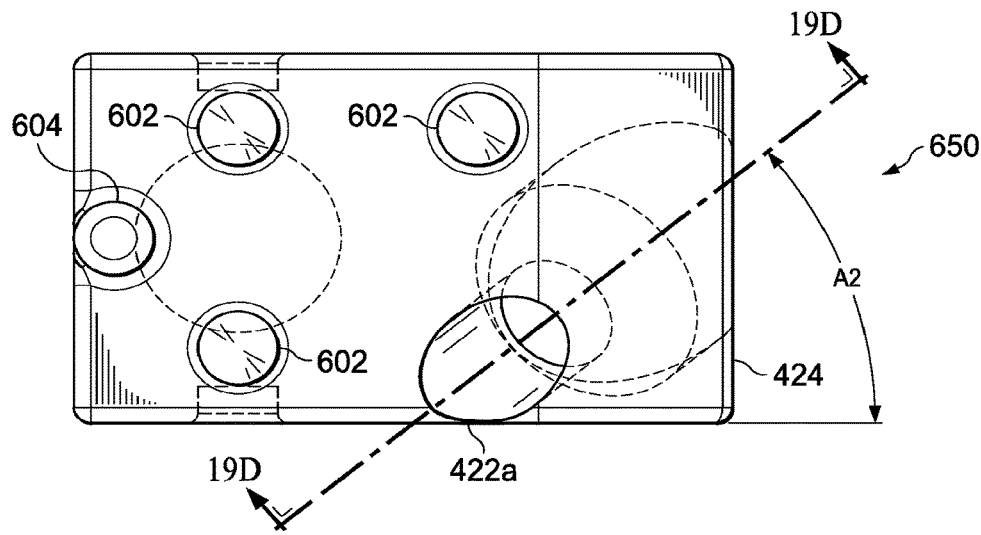
Figure 19D:
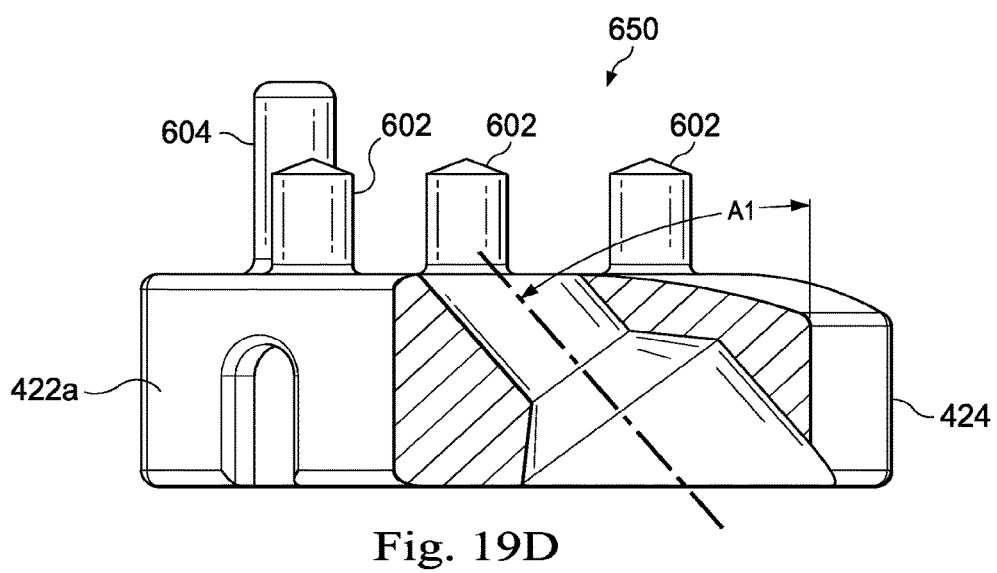
Figure 20A:
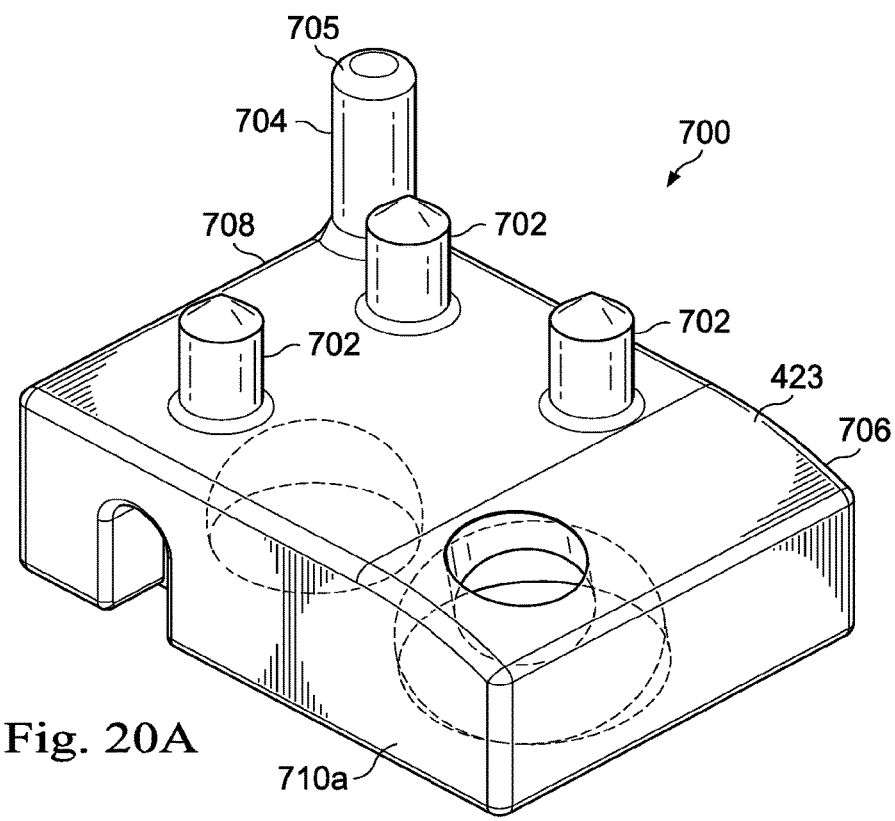
FIGS. 20A-20D illustrate views of an exemplary jig of the posterior cervical stabilization system in accordance with various aspects of the disclosure.
Figure 20B:
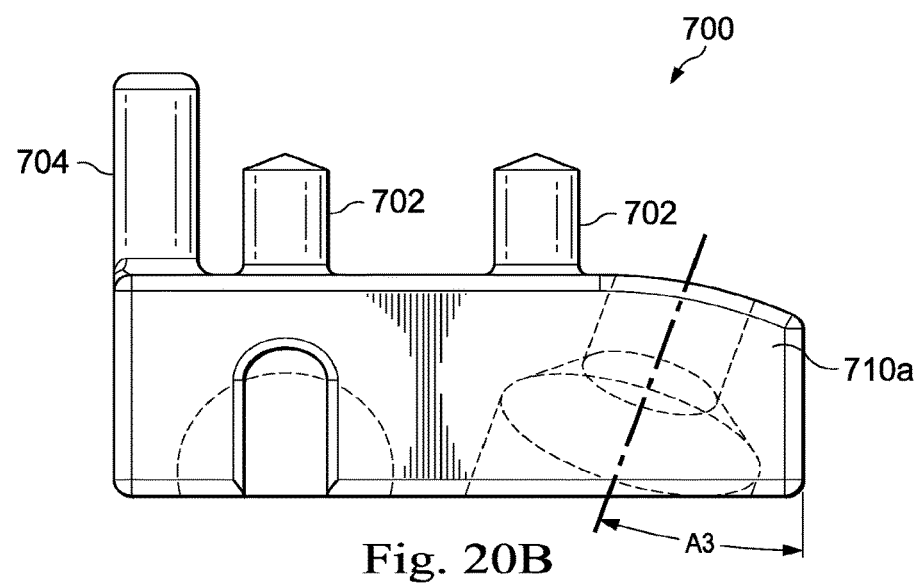
Figure 20C:
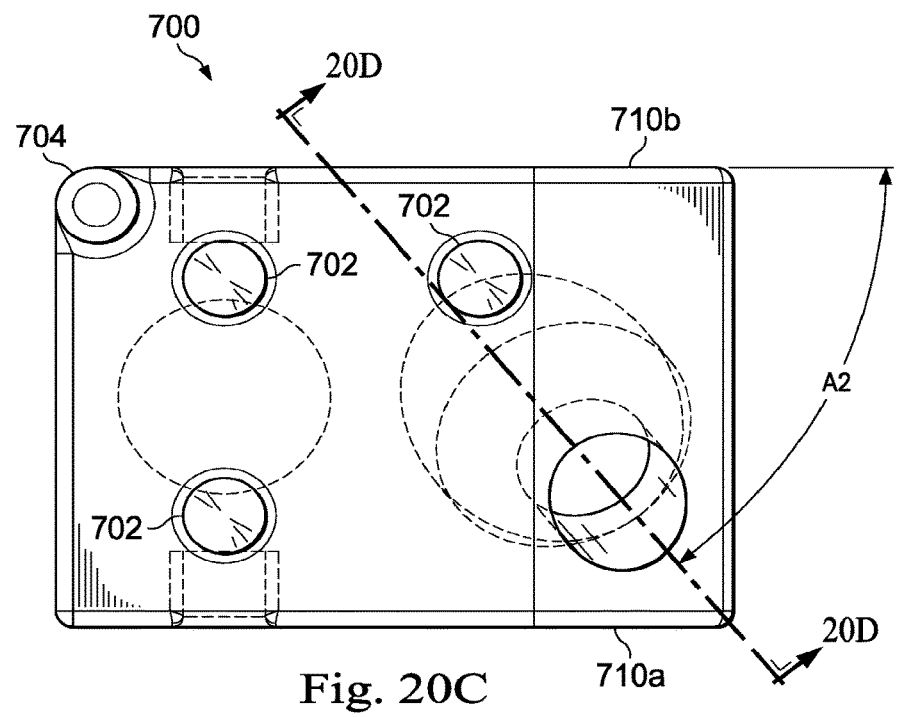
Figure 20D:
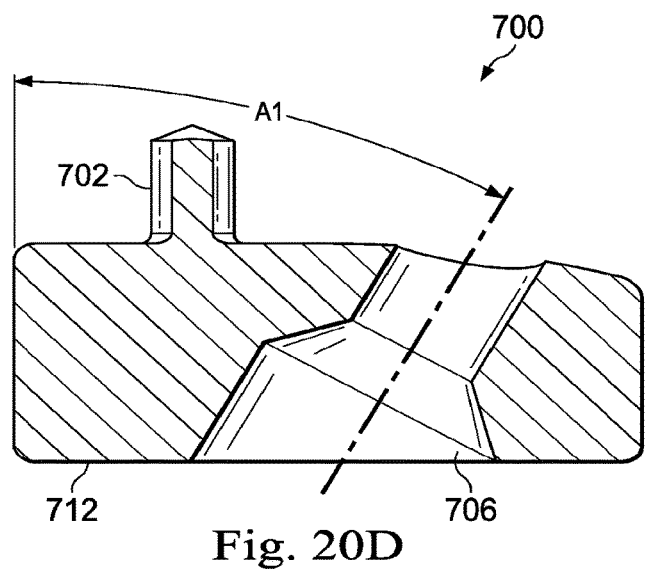

FIGS. 16A-16C show the rod connector 406. In this embodiment, the rod connector 406 is a separate element from the jig 402 and provides multi-axial pivot capability to the system. It includes a pivot head 470 and a U-shaped receiver 472, connected by a narrow neck 474. A longitudinal centerline 476 extends through the head 470, neck 474, and receiver 472.

The pivot head 470 is shaped as a spherical head having a flat band 480 formed thereon, forming a cylindrical portion having a longitudinal axis 482. The longitudinal axis 482 of the flat band 480 is disposed at an angle β relative to the centerline 476. In some embodiments, the angle β is within the range of about 20-40 degrees. In other embodiments, the angle β is within the range of about 28-35 degrees. In other embodiments, the angle β is about 30 degrees. The spherical portion of the head 470 has a diameter sized greater than the opening 432 of the attachment feature 433, while the flat band 480 has a diameter sized less than the opening 432 of the attachment feature 433. Accordingly, when the head 470 is angled so that flat band 480 lies in a plane parallel to the outwardly facing side 420 or parallel to the plane defined by the opening 432, the head 470 may pass through the opening 432 of the attachment feature 433. With the head 470 within the attachment feature 433, the rod connector 406 may be pivoted so that the flat band 480 is not within a plane parallel to the outwardly facing side 420 or the opening 432. In this position, the head 470 is pivotably captured within the attachment feature 433 by virtue of the larger diameter spherical portion. In addition, the head 470 may pivot within attachment feature 432 so long as the band 480 does not become parallel to the outwardly facing side 420.

The receiver 406 is configured to receive a fixation rod. It is U-shaped with two extending arms 490 connected a partially cylindrical bottom portion 492. The bottom portion 492 is configured to interface with the curved outer surface of a cylindrical fixation rod as shown in FIGS. 12 and 13. In the embodiments shown, the bottom portion 492 includes a diameter within a range of about 3-4 mm. In one example, the bottom portion 492 has a diameter of about 3.7 mm. Other sizes are also contemplated and the size of the bottom portion 492 may be selected to correspond to the expected size of the fixation rod. Other embodiments include a bottom portion having a square shape, with teeth, or with other arrangements to engage the fixation rods. Each arm 490 of the receiver 472 includes a threaded inner surface 494 configured to enable threading of the set screw 408. The outer surface of the arms 490 may taper in a conical manner. For example, the receiver 472 may have a bottom region adjacent the neck having a larger diameter or size than the diameter or size of the receiver 472 along the top edge of the arms 490. In one embodiment, the receiver has a diameter of about 8.5 mm at the bottom region and about 7.7 mm at the top of the arms. The receiver 472 may be sized so that the distance between the center of the spherical head 470 and the top of the arms 490 is within the range of about 8-15 mm. In one embodiment, the range is within about 11-13 mm.

Again, since the system can be used on the cervical vertebrae, the height limitations may be minimized. However other sizes, larger and smaller may be utilized.

In the embodiment shown, the flat band 480 is aligned so that the receiver 472 can tip forward and aft about the pivot head in the direction of the longitudinal axis of a rod seated on the bottom portion 492 within the receiver without concern for removal of the receiver from the jig 402.

Figure 17:
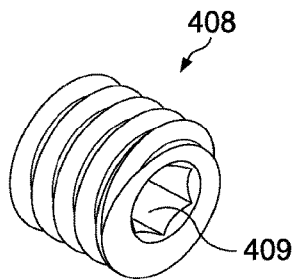
FIG. 17 illustrates an isometric view of an exemplary set screw of the posterior cervical stabilization system of FIG. 12 in accordance with various aspects of the disclosure.

FIG. 17 shows the set screw 408 in greater detail. It includes a hex tool engaging recess 409 and is sized to thread between the arms 490 of the receiver 472 to capture a rod within the receiver and prevent inadvertent removal.

It should be understood that although the systems disclosed herein are discussed as being used with the cervical region of the spine, the systems may be utilized in all regions of the spine, including the cervical, thoracic, lumbar, and lumbo-sacral regions. It should also be understood that the systems may extend across a spinal motion segment having only two vertebrae or more than two vertebrae by combining multiple jigs with a fixation rod as shown in FIGS. 1-7 with each jig attached to a separate vertebra. In some embodiments, two or more stabilization systems may be employed simultaneously along the same spinal motion segment.

In some embodiments, the system 400 described above forms a part of a set of systems cooperate together to treat a spinal condition. For example, in some embodiments, multiple jigs 402 may be attached to different vertebrae, whether adjacent or not, and a fixation rod may connect all the jigs. Some embodiments include a plurality of jigs of a set each designed to fit one or more particular vertebrae. FIGS. 18-21 show a plurality of different systems shaped for particular vertebrae that may be packaged, used, or sold as a set for treating a particular condition. In addition, the jig 402 also may include as a part of a set in combination with these systems disclosed herein.

Figure 21A:
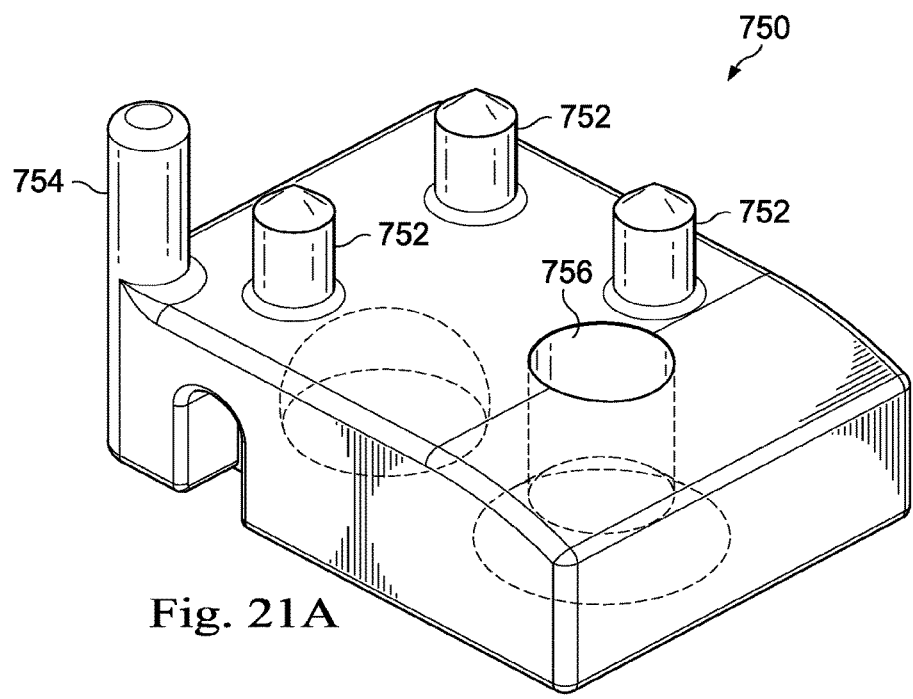
FIGS. 21A-21C illustrate views of an exemplary jig of the posterior cervical stabilization system in accordance with various aspects of the disclosure.
Figure 21B:
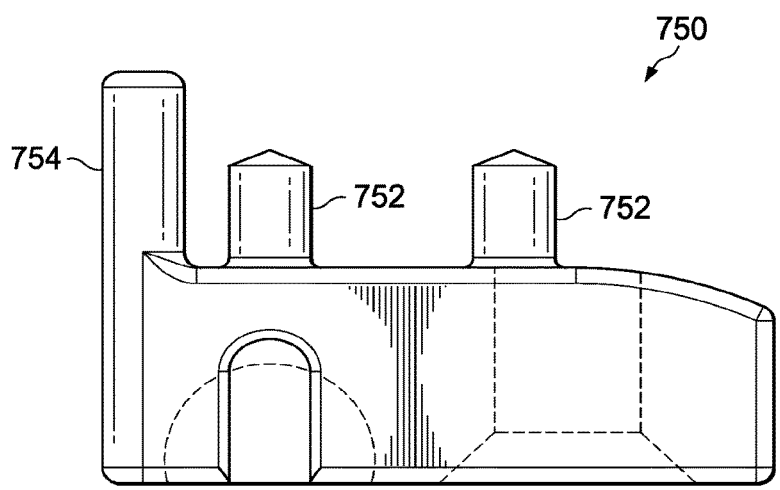
Figure 21C:
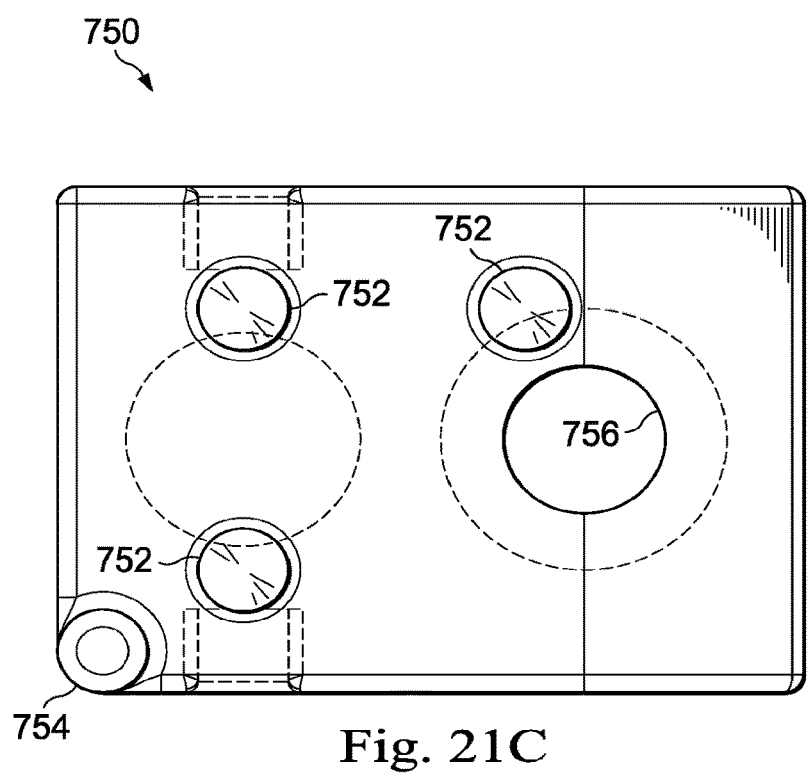

FIGS. 18A-18E show an exemplary alternative jig 600 usable on any vertebra, but particularly suited for use on C2-C6 vertebrae, and FIGS. 19A-19D show an exemplary jig 650 usable on any vertebra, but particularly suited for use on a C7 vertebra. FIGS. 20A-20D show an exemplary jig 700 usable on any vertebra, but particularly suited for use on C7 vertebra, and FIGS. 21A-21C show an exemplary jig 750 usable on any vertebra, but particularly suited for use on a T1 vertebra. The jigs may be used with the fasteners, rod connector, and set screws disclosed above. Those descriptions will not be repeated here.

Referring first to FIGS. 18A-18E, the jig 600 include many features similar to the jig 402 discussed above. Since the discussion above applies, those discussions will not be repeated here. The jig 600 however includes different protruding features, including different penetrating features 602 and a different lateral bone outrigger 604. In this embodiment, the penetrating features 602 are formed as extending cylinders having pointed, conical ends. The pointed ends are configured to penetrate the exterior of the lateral mass but because the angle of the conical end is less acute than the angle of the conical end of the penetrating features 450 in FIG. 14A-14E, the system may be sturdier over time. In addition, loads applied laterally on the jig 600 may result in loading that is closer to a normal direction on the cylindrical surfaces of the penetrating features 602 in the bone than in the conical surfaces of the penetrating features 450.

The lateral bone outrigger 604 in this embodiment is also a single cylindrical feature. The cylindrical feature is disposed substantially along the centerline of the jig 600. This lateral bone outrigger 604 has a bone-abutting surface 606 on its medial side and/or end. The lateral bone outrigger 604 is formed with a radius between the sides and ends to provide a smooth surface to abut against the lateral side of the lateral mass.

Also in this embodiment, the angle A1 may be in the range of about 30 degrees and may correspond within a degree to the angle A2. These angles may vary as discussed with reference to the jig 402 above.

FIGS. 19A-19D show a jig 650 particularly shaped for use on C7 vertebra. The jig 650 is similar to those described above in many respects, but its bore is angled differently to accommodate the shape of the lateral mass of the C7 vertebra. In this embodiment, the angle A1 may be in the range of about 34 degrees and may correspond within less than about 10 degrees to the angle A2. The angle A2 may be within a range of about 35-45 degrees, and may about 40 degrees. These angles may vary as discussed with reference to the jig 402 above.

FIGS. 20A-20D show another embodiment of a jig 700 particularly shaped for use on a C7 vertebra. Like the embodiments above, the jig 700 includes protruding features that include penetrating features 702 and lateral bone outrigger 704 and a fastener bore, referenced herein by the numeral 706. In this embodiment, the lateral bone outrigger 704 is a cylindrical protrusion having a bone abutting surface 705 formed of a radius at an end that is configured to abut against the lateral mass as described above. In this example however, the lateral bone outrigger 704 protrudes at a corner of the inwardly facing surface. In this example, the cylindrical lateral bone outrigger surface is flush with both the lateral end 708 of the jig 700 and one of the side edges 710. This may provide additional stability to the jig on a C7 vertebra of particular patients with a pedicle fastener in place of a lateral mass fastener.

Particularly, the jig 700 is formed so that the fastener bore 706 is angled away from the lateral bone outriggers 704. In this embodiment, the fastener bore opening 712 is contained entirely within the outwardly facing side and the bore 706 exits the inwardly facing side in the curved surface portion 714.

In this embodiment, the angle A1 may be in the range of about 33 degrees and leading away from the lateral bone outrigger 704. Likewise, the angle A2 may be about 53 degrees. In the embodiment shown the bore 430 is angled when taken in cross-section at an angle A1 within a range of about 20-55 degrees for example. In some embodiments, the angle A1 is within a range of about 25-45 degrees, and in yet other embodiments, the angle A1 is within a range of about 26-41 degrees. Some embodiments have an angle A1 about 32 degrees.

In addition, in the embodiment shown, the bore 712 is angled relative to the side edge 710b at an angle A2 within a range of about 30-65 degrees for example. Here, the angles A2 and A3 may be negative angles when compared to the embodiments discussed above. In some embodiments, the angle A2 is within a range of about 45-60 degrees, and in yet other embodiments, the angle A2 is within a range of about 50-55 degrees. Some embodiments have an angle A2 about 53 degrees.

In addition, the overall width between side edges of the jig 700 is larger than the overall width between side edges of the jigs 600 and 650 described above. In this example, the jig width may be within the range of about 6-15 mm, and in some embodiments within a range of 11-13 mm.

FIGS. 21A-21C show another embodiment of a jig 750 particularly shaped for use on a T1 vertebra. Like the embodiments above, the jig 750 includes protruding features that include penetrating features 752 and a lateral bone outrigger 754 and a fastener bore, referenced herein by the numeral 756. In this example however, since the jig 750 is shaped to correspond to the shape of a T1 vertebra, the lateral bone outrigger 754 is disposed at an opposite side edge of the lateral end 758 of the jig 750 at a corner of the inwardly facing surface. In this example, the cylindrical facing surface is flush with both the lateral end 708 of the jig 700 and one of the side edges 710. This may provide additional stability to the jig on the T1 vertebra.

In addition, the fastener bore 756 is directed straight through or substantially perpendicular to the planes of the inwardly and outwardly facing surfaces. Accordingly, because of the shape of the T1 vertebra, the fastener may penetrate the pedicle of the T1 vertebra.

As described above, some embodiments include a set of jigs that may include any two or more of the jigs and systems discussed above. In one example, the set may include a plurality of jigs including one or more jigs as shown in FIGS. 14A-14E or FIGS. 18A-18E, one or more jigs as shown in FIGS. 19A-19D and 20A-20D, and one or more jigs as shown in FIG. 21A-21C. Other combinations of jigs are contemplated.

Figure 22A:
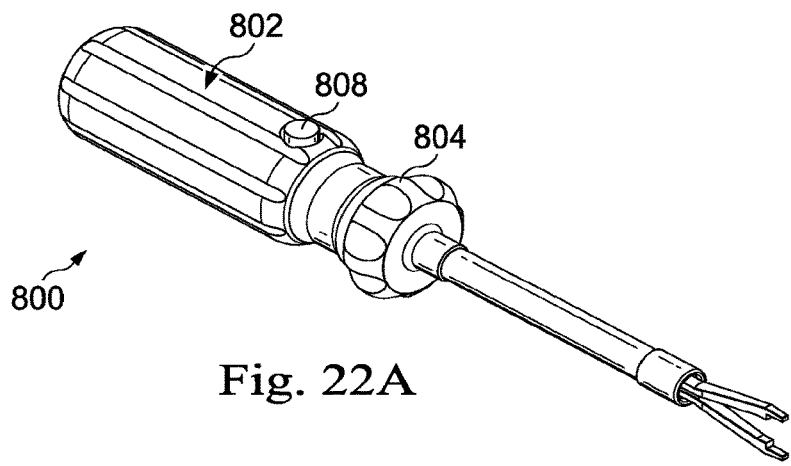
FIGS. 22A and 22B illustrate views of an exemplary surgical instrument of the posterior cervical stabilization system in accordance with various aspects of the disclosure.
Figure 22B:
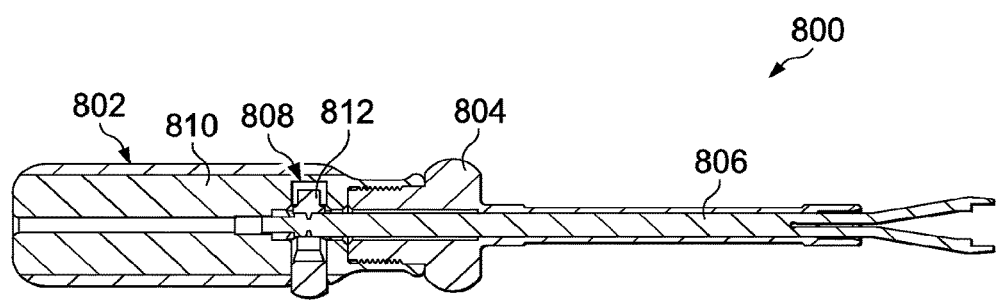

FIGS. 22A and 22B illustrate an exemplary surgical introducer 800 that may be used during the implantation process to introduce the jig to a surgical site during a surgical procedure. The introducer includes a handle grip 802, a tube 804, a shaft 806, a button 808, a handle core 810, and a spring 812.

The shaft 806 includes a proximal end having an annular notch therein and a distal end that is bifurcated into two cooperating fingers that are sized and spaced to engage the instrument engaging features 434 in each side edge of the jig. The button 808 includes a passage through which the proximal end of the shaft 806 passes. Within the passage, the button 808 includes a projecting mechanical stop that selectively fits within the annular notch on the proximal end of the shaft 806. The spring 812 biases the button to a position where the stop is disposed within the annular notch when the shaft is inserted within the handle. The shaft 806 can be removed by pressing the button 808 to remove the stop from the annular notch.

As can be seen, the tube 804 extends about the shaft 808 and threadedly connects to the handle core 810. Threading and unthreading the tube 804 results in the tube 804 travelling along the shaft 808. Accordingly, by unthreading the tube 804, the tube 804 can travel along the shaft 808 and limit the separation achieved by the fingers of the shaft 808. Likewise, the tube 804 can be used to tighten the fingers onto a jig as desired.

In use, the posterior stabilization system may be implanted with the fixation rod as part of an orthopedic system. To do this, one or more surgical exposures are made proximate to an area of the spine or other bones to be instrumented. The surgical exposures may be open, minimally-invasive, or of other types that are known in surgical practice. The vertebrae or other surgical site is prepared, for example by retracting tissue, removing tissue, adjusting bony or other tissue, and/or other steps to prepare and fixate a bone or bones. Some embodiments include drilling pilot holes to be used to introduce the bone penetrating features protruding from the jig. This may be done using a guide or using other known technique.

Once the surgical site is prepared, the jig may be introduced into the surgical site. In some embodiments, this may include first selecting a single jig from a plurality of jigs designed to correspond to particular vertebra. For example, one jig may correspond to C2-C6 vertebrae, while a separate jig may correspond to a C7 vertebra, and a further jig may correspond to a T1 vertebra. With the proper jig selected, the surgeon may grasp the jig with the surgical instrument 800 along the instrument engaging features 434. The surgeon may tighten the fingers of the instrument upon the selected jig by threading the tube 804 until the distal end of the tube 804 begins to clamp on the fingers of the shaft 806. When the jig firmly grasped, the jig is then introduced to the surgical site by pressing the jig against the lamina of the vertebra. As the penetrating features penetrate the vertebra, the lateral bone outrigger engages the lateral side of the posterior vertebra. The jig may be before advanced until the bone abutting surface portion 448 of the inwardly facing side of the jig engages the lamina along a medial portion while the lateral bone outrigger engages a lateral potion of the vertebra.

With the jig stabilized by the penetrating features in the lamina, the jig may be used as a guide to further prepare the vertebra to receive the fastener. In some embodiments, a pilot hole or bore is drilled, tapped, punched, or otherwise created in the vertebra for receiving the fastener. In some embodiments, the fastener is a self-drilling or self-tapping screw, and predrilling an opening may be omitted. In embodiments using the jigs 400, 600, and 650, the hole may be formed in the lateral mass in the direction of the lateral bone outrigger. Also, depending on the embodiment used, the hole may be formed at an angle corresponding to the fastener bore, and in one embodiment, may be about at an oblique angle in any of the angles described above.

The fastener 404 may then be introduced into the created pilot hole. An appropriate surgical tool or driver is engaged with the tool-engaging recess 468 of the fastener 404. As the fastener is tightened to the bone, the force may apply additional loading, further pressing the protruding features into the bone structures. As such, the lateral bone outrigger engages the lateral side of the vertebra with its end and/or the medial side of the lateral bone outrigger.

The jig is now secured in place with the lateral bone outrigger along on the lateral side of the lateral mass and with the curved surface portion of the inwardly facing side on the lamina. The fastener and the penetrating features affix the jig in place. With the jig in place, the introducer instrument 800 may be removed by loosening the tube 804 by threading it with the handle so that it moves proximally away from the fingers of the shaft 806.

The rod connector 406 is then introduced to the implanted jig. To do this, the rod connector 406 is oriented so that the flat band 480 can pass through the opening 432 in the outwardly facing surface and into the attachment feature 433 in the top side. As described above, this may be accomplished by orienting the flat band 480 into a plane that is substantially parallel to a plane defined by the edge of the opening 432 to the attachment feature 433 in the outwardly facing side of the jig. After passing the pivot head 470 into the attachment feature 433, the rod connector 406 may be rotated so that the flat band 480 is not within a plane that is substantially parallel to a plane defined by the edge of the opening 432 to the attachment feature 433. The rod connector 406 may then be pivotably attached to the jig. The surgeon may then make any desired adjustments to the orientation of saddle 14 with respect to bone anchor 18. For example, the surgeon may rotate or angle the saddle 14 relative to the bone anchor 18 to achieve a desired orientation to accommodate reception of a fixation rod.

The process is then repeated for one or more additional vertebra, either adjacent or spaced from the first treated vertebra.

When the rod connectors are properly oriented, a fixation rod may be introduced into the channels of the receivers 472. The rod may is inserted towards the bottom portion of the receiver at least to a point so that the set screw 408 can threadingly engage the threaded arms 490 of the receiver to hold the rod within the receiver.

When the spine and fixation elements are positioned as the surgeon desires, the rod is locked within the channel of the receiver by advancing the set screw 408 against the rod. As the set screw 408 is advanced it urges the rod towards the bottom portion of the receiver until the fixation rod is locked in place between the set screw and the bottom of the receiver.

FIGS. 23-28 show an additional embodiment of a system 800. Since the system includes many similarities to the other embodiments described herein, not all features will be re-addressed recognizing that the descriptions above also apply to the system 800. The system includes a jig 802, a head 804 configured to connect to a rod connector 806, and a fastener 808. Like the other embodiments shown and described herein, the jig 802 includes curved or rounded corners and surfaces. The jig 802 however is more ergonomically shaped and includes more pronounced curved or rounded corners and surfaces. In addition, the jig connects with the head 804 carried on the jig 802, rather than being a part of the receiver. This will be more apparent in the discussion below.

The jig 802 includes an outwardly facing top side 810, an internally facing bottom side 812, two side edges 814*a*, 814*b*, a medial end 816 configured to be medially disposed when implanted on a vertebra, and a lateral end 818 configured to be laterally disposed when implanted on a vertebra. The outwardly facing side 810 of the jig 802 is substantially flat and includes a fastener opening 822 leading to a bore 824 similar to those described above, angled in the manner described with reference to other embodiments herein, that receives the fastener 808. The jig 802 and all other embodiments of jigs disclosed herein, include a fastener bore where a cross-section through the bore 430 shows the bore 430 angled at an angle A1 within a range of about 5-55 degrees for example. In some embodiments, the angle A1 is within a range of about 10-45 degrees, and in yet other embodiments, the angle A1 is within a range of about 10-41 degrees. In addition, in some embodiments, the jig 802 and all other embodiments of jigs disclosed herein, include a fastener bore angled relative to the side of the jig at an angle A2 within a range of about 5-55 degrees for example. In some embodiments, the angle A2 is within a range of about 10-45 degrees, and in yet other embodiments, the angle A2 is within a range of about 10-41 degrees. In addition, angle A3 representing the angle of the bore looking into the axial plane or from the medial end of the jig 802 and all other embodiments of jigs disclosed herein is within a range of about 5-55 degrees. In some embodiments, the angle A3 is within a range of about 10-45 degrees, and in yet other embodiments, the angle A3 is within a range of about 10-41 degrees.

In the exemplary embodiment shown, the outwardly facing side 810 carries the head 204, which protrudes from the outwardly facing top side 810.

Figure 23:
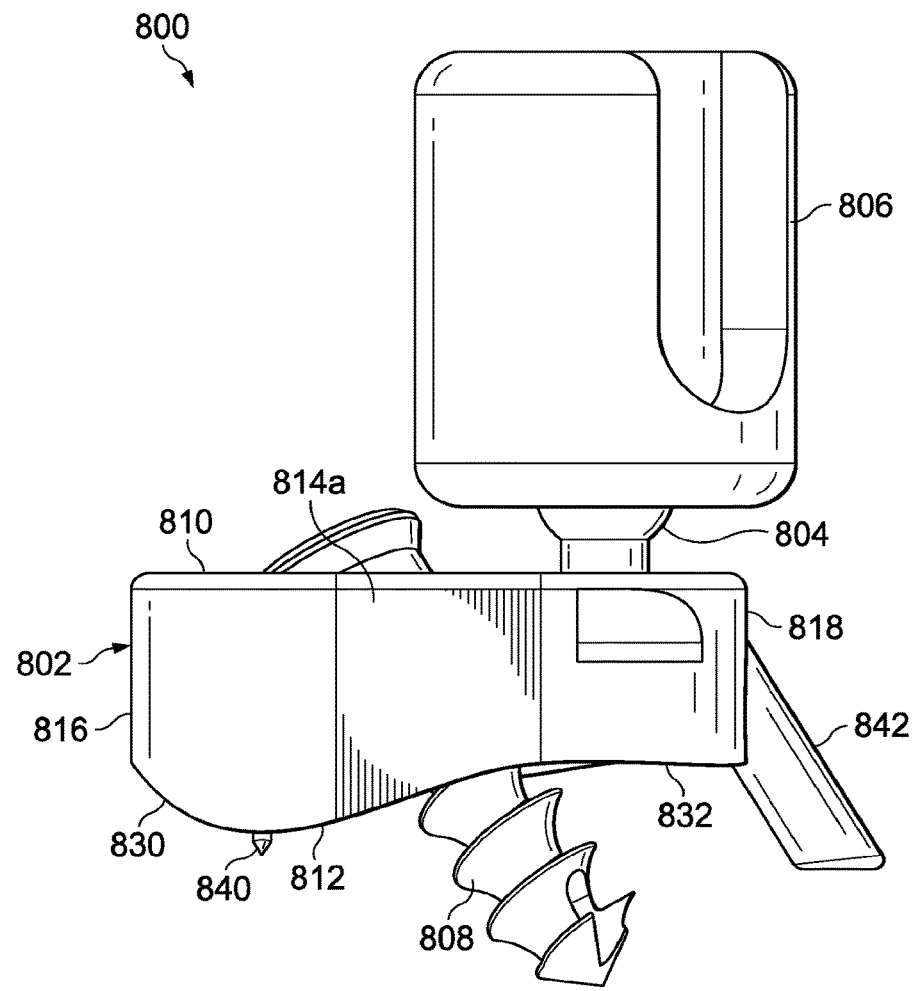
FIGS. 23 and 24 illustrate opposing side views of another posterior cervical stabilization system in accordance with various aspects of the disclosure.
Figure 24:
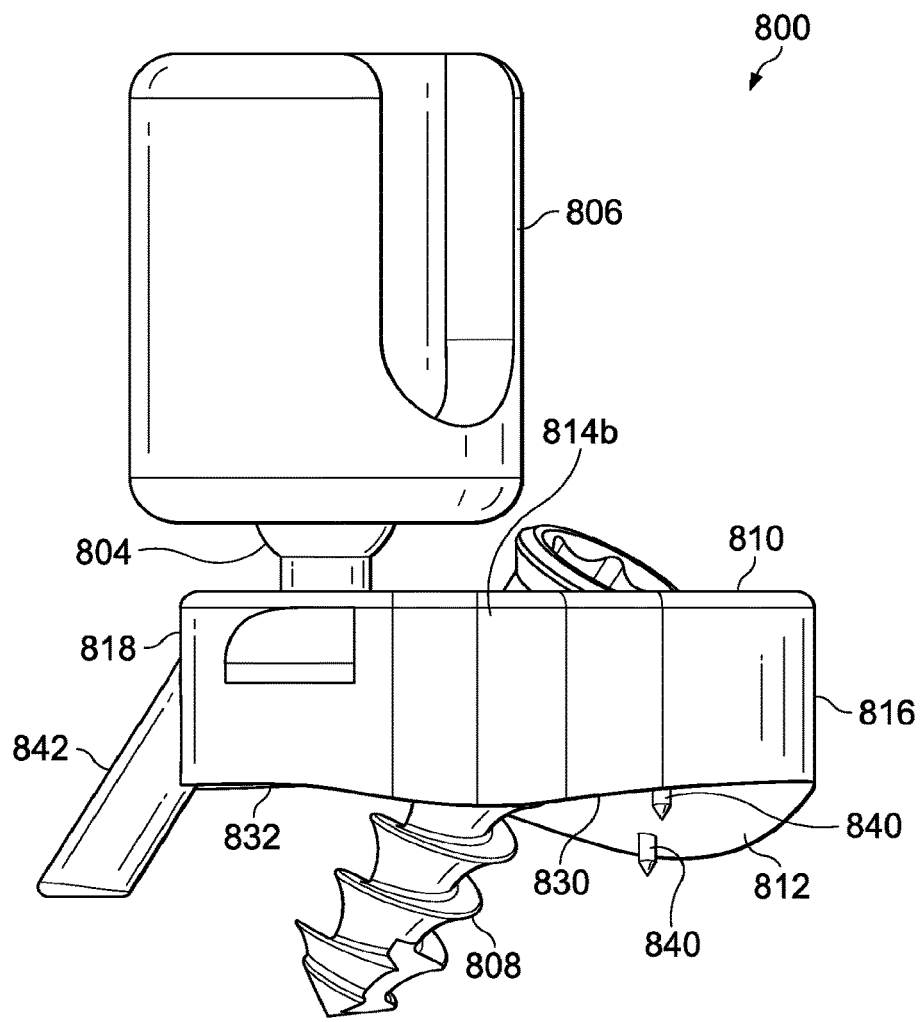
Figure 27:
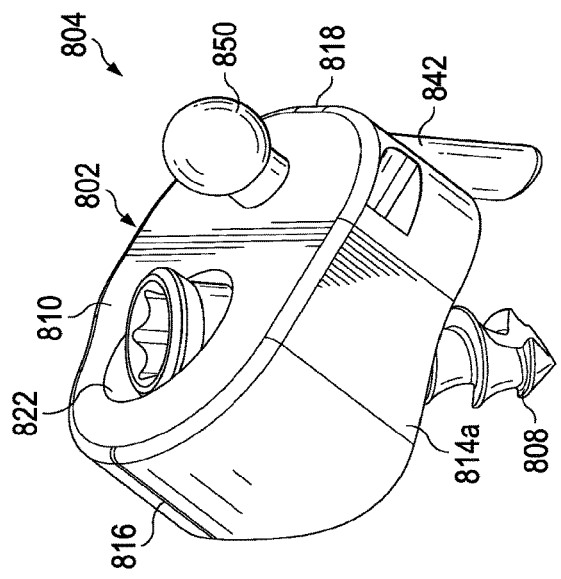
FIG. 27 illustrates an isometric view of a jig with a pivot head and a fastener of the posterior cervical stabilization system of FIGS. 23 and 24 in accordance with various aspects of the disclosure.
Figure 26:
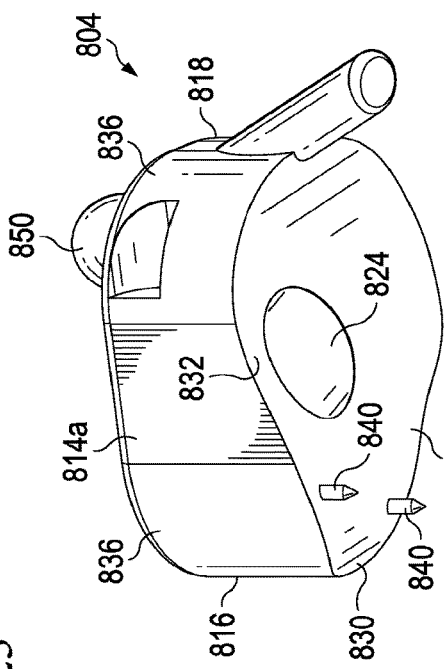
FIGS. 25 and 26 illustrate views of a jig with a pivot head of the posterior cervical stabilization system of FIGS. 23 and 24 in accordance with various aspects of the disclosure.
Figure 25:
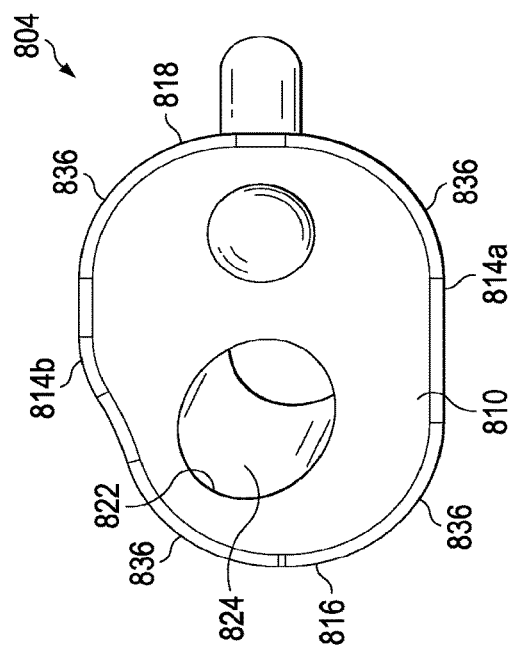

The internally facing bottom side 812 is curvilinear and, like the embodiments above, includes a relatively tapered surface portion or curved surface portion 830 disposed toward the medial end 816 of the jig 802. Here, the internally facing bottom side 812 also includes a laterally curvilinear surface shaped and arranged to interface with the shape of natural bone. Using the outwardly facing top side 810 as a reference, the internally facing bottom side 812 generally curves from a region of greater thickness at the medial side 816 to a region of less thickness at the lateral side 818. As best seen in FIG. 23, the internally facing bottom side 812 includes an edge extending from the medial side 816 in the rounded convex curved surface portion 830, to a rounded concave surface portion 832. FIG. 24 shows the opposing side, where the curves are less pronounced, but the curve includes the rounded convex curved surface portion 830, to the rounded concave surface portion 832.

The jig 802 includes rounded edges 836 between the side edges 814*a*, 814*b* and the medial and lateral ends 816, 818 having a larger radius than the radius of the rounded edges shown in the drawings of the other embodiments herein. Here, the rounded edges 836 can be seen in the top view of the jig 802 shown in FIG. 25. In addition, in this embodiment, the side edge 814 incrementally tapers inwardly from the medial side to the lateral side 818, including both concave and convex sections. This helps the jig more fully conform to the underlying bone structure of the underlying vertebra.

The bottom side 812 is shaped to more closely match the shape of the bone structure and therefore is a non-planar structure. Protruding from the bottom surface, the jig 852 includes penetrating features 840 and a different lateral bone outrigger 842. In this embodiment the penetrating features 840 are conical pins or small spikes as described above. The penetrating features 840 can be used to temporarily hold the modules to a lateral mass bone prior to the creation of fastener holes for receiving the fastener. The outrigger 842 is substantially centrally disposed at the lateral end 818 and extends at an oblique angle in the lateral direction from the bottom surface 812, and also at an angle from the penetrating features 840. Here, the outrigger 842 extends at an angle within a range of about 20-60 degrees. In some embodiments, the range is about 25-40 degrees, and in some embodiment, the angle is about 35 degrees.

The head 804 may be formed of a spherical head portion 850 and a post portion 852, with the spherical head portion 850 disposed on the post portion 852. The head portion 850 and post portion 852 may be formed together of a monolithic material, or the post portion 852 may be secured to the head portion 850 in any manner. The post portion 852 may be fit within a post bore formed in the jig 802. The receiver 806 is configured to swivel and pivot on the head portion 850.

The receiver 806 includes a through hole in its bottom portion that receives and swivels on the head portion 850 while maintaining a connection between the receiver 806 and the head portion 850. Additional details of the receiver will not be repeated here since they were described previously.

Figure 28:
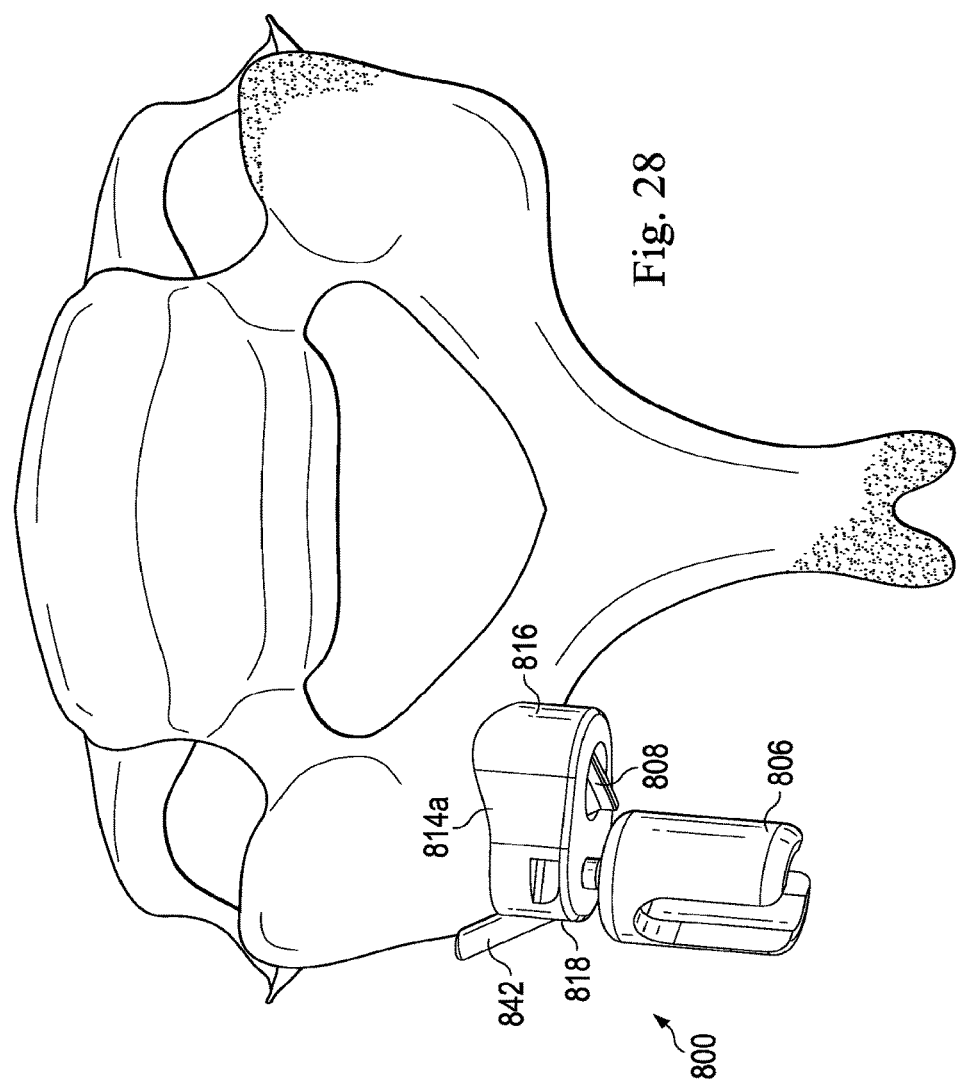
FIG. 28 illustrates a top view of the exemplary posterior cervical stabilization system of FIGS. 23 and 24 in place on a vertebra in accordance with various aspects of the disclosure.

FIG. 28 shows the system 800 disposed on a vertebra. As can be seen, the system 800 abuts against the bone, and the outrigger extends along a side of the bone structure to provide stabilizing support to the jig 802. In some embodiments, like those described above, the left and right jigs configured for respective attachment to left and right sides of the vertebra, are mirror images of each other. That is, the non-symmetric features of any jig are mirrored to the opposing jig.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. It has obvious implications in major complex revision and other reconstructive hip arthroplasty procedures.

I claim:

1. An implantable body for a posterior stabilization system comprising:
    a lateral end, a medial end, an inwardly facing surface, and an outwardly facing surface, the inwardly facing surface having a bone-abutting portion disposed proximate the medial end and configured to abut against a lamina when the body is implanted along a vertebra;
    a lateral bone outrigger extending from the inwardly facing surface adjacent the lateral end, the lateral bone outrigger having a bone-abutting surface along a medial portion disposed to abut against a lateral mass of the vertebra when the body is implanted along a vertebra, the lateral bone outrigger having a first height;
    a penetrating feature extending from the inwardly facing surface between the bone-engaging portion of the inwardly facing surface and the lateral bone outrigger, the penetrating feature having a second height less than the first height; and
    a fastener bore extending through the body from the inwardly facing surface to the outwardly facing surface, the fastener bore being angled toward the lateral bone outrigger.

2. The implantable body of claim 1, wherein the inwardly facing surface comprises a tapered surface and a flat surface, the bone-abutting portion being formed of the tapered surface.

3. The implantable body of claim 1, wherein the inwardly facing surface comprises a curved surface and a flat surface, the bone-abutting portion being formed of the curved surface.

4. The implantable body of claim 1, wherein the bone-abutting surface on the lateral bone outrigger is a rounded surface.

5. The implantable body of claim 1, wherein the fastener bore is angled at an angle within the range of about 20-55 degrees when measured in cross-section.

6. The implantable body of claim 5, wherein the fastener bore is angled at an angle within the range of about 20-55 degrees as measured from a side edge.

7. The implantable body of claim 6, wherein the second height from the inwardly facing surface is within a range of about 4-8 mm.

8. The implantable body of claim 6, wherein the lateral bone outrigger is cylindrically shaped and is disposed proximate only a portion of the lateral end.

9. The implantable body of claim 6, wherein the lateral bone outrigger is disposed in a corner of the inwardly facing surface.

10. The implantable body of claim 6, wherein the lateral bone outrigger is disposed along a centerline extending from the medial end to the lateral end.

11. The implantable body of claim 1, wherein the fastener bore is angled so that when the implantable is implanted, the fastener bore forms an angle in the range of 20-55 degrees from the sagittal plane and an angle in the range of 20-55 degrees from the axial plane.

12. A posterior stabilization system comprising:
    an implantable body shaped to abut against a lateral mass of a cervical vertebra comprising:
        a lateral end, a medial end, an inwardly facing surface and an outwardly facing surface, the inwardly facing surface having a bone-abutting portion disposed proximate the medial end configured to abut against a lamina when the body is implanted along a vertebra;
        a lateral bone outrigger extending from the inwardly facing surface adjacent the lateral end, the lateral bone outrigger having a bone-abutting surface along a medial portion disposed to abut against a lateral mass of the vertebra when the body is implanted along a vertebra;
        a penetrating feature extending from the inwardly facing surface between the bone-engaging portion of the inwardly facing surface and the lateral bone outrigger; and
        a fastener bore extending through the body from the inwardly facing surface to the outwardly facing surface;
    a rod receiving portion sized to receive a fixation rod, the rod receiving portion being pivotably attached to the body; and
    a fastener sized to extend through the bore and penetrate the lateral mass of the vertebra.

13. The system of claim 12, wherein the inwardly facing surface comprises a curved surface and a flat surface, the bone-abutting portion being formed of the curved surface.

14. The system of claim 12, wherein the bone-abutting surface on the lateral bone outrigger is a rounded surface.

15. The system of claim 12, wherein the fastener bore is angled at an angle within the range of about 20-55 degrees when measured in cross-section.

16. The system of claim 12, wherein the fastener bore is angled at an angle within the range of about 20-55 degrees as measured from a side edge.

17. A non-pedicle based fixation system, comprising
    a first posterior stabilization system comprising:
        a first body shaped to abut against a lateral mass of a first cervical vertebra, the first body comprising:
            a lateral end, a medial end, an inwardly facing surface, and an outwardly facing surface, the inwardly facing surface having a bone-abutting portion disposed proximate the medial end and configured to abut against a lamina when the body is implanted along a vertebra;
            a lateral bone outrigger extending from the inwardly facing surface adjacent the lateral end, the lateral bone outrigger having a bone-abutting surface at along a medial portion disposed to abut against a lateral mass of the vertebra when the body is implanted along a vertebra, the lateral bone outrigger having a first height; and
            a penetrating feature extending from the inwardly facing surface between the bone-engaging portion of the inwardly facing surface and the lateral bone outrigger, the penetrating feature having a second height less than the first height; and
        a first rod receiving portion shaped to receive a fixation rod, the rod receiving portion being disposed closer to the lateral end than the medial end;
    a second posterior stabilization system comprising
        a second body shaped to abut against a lateral mass of a second cervical vertebra, the first body comprising
            a lateral end, a medial end, an inwardly facing surface, and an outwardly facing surface, the inwardly facing surface having a bone-abutting portion disposed proximate the medial end and configured to abut against a lamina when the body is implanted along a vertebra;

a lateral bone outrigger extending from the inwardly facing surface adjacent the lateral end, the lateral bone outrigger having a bone-abutting surface at along a medial portion disposed to abut against a lateral mass of the vertebra when the body is implanted along a vertebra, the lateral bone outrigger having a first height;

a penetrating feature extending from the inwardly facing surface between the bone-engaging portion of the inwardly facing surface and the lateral bone outrigger, the penetrating feature having a second height less than the first height; and a second rod receiving portion shaped to receive the fixation rod, the rod receiving portion being disposed closer to the lateral end than the medial end; and a fixation rod disposed within the first and second rod receiving portions.

18. The system of claim 17, wherein the first body comprises a fastener bore extending through the body from the inwardly facing surface to the outwardly facing surface, the fastener bore being angled toward the lateral bone outrigger.

19. The system of claim 18, wherein the first body includes a side edge, the fastener bore being angled away from the side edge.

20. The system of claim 19, wherein the fastener bore is angled toward the lateral bone outrigger within an angle range of about 20-55 degrees, and the fastener bore angled away from the side edge within an angle range of about 20-55 degrees.

* * * * *